US008158643B2

(12) United States Patent
Andrés-Gil et al.

(10) Patent No.: US 8,158,643 B2
(45) Date of Patent: Apr. 17, 2012

(54) SUBSTITUTED DIAZA-SPIRO-PYRIDINONE DERIVATIVES FOR USE IN MCH-1 MEDIATED DISEASES

(75) Inventors: José Ignacio Andrés-Gil, Madrid (ES); Manuel Jesús Alcázar-Vaca, Toledo (ES); Frank Matthias Dautzenberg, Vosselaar (BE); Joannes Theodorus Maria Linders, Eindhoven (BE)

(73) Assignee: Janssen Pharmaceutica N.V. (BE)

( * ) Notice: Subject to any disclaimer, the term of this patent is extended or adjusted under 35 U.S.C. 154(b) by 292 days.

(21) Appl. No.: 12/444,878

(22) PCT Filed: Dec. 4, 2007

(86) PCT No.: PCT/EP2007/063310
§ 371 (c)(1),
(2), (4) Date: Apr. 9, 2009

(87) PCT Pub. No.: WO2008/068265
PCT Pub. Date: Jun. 12, 2008

(65) Prior Publication Data
US 2010/0035909 A1      Feb. 11, 2010

(30) Foreign Application Priority Data
Dec. 5, 2006    (EP) .................................... 06125421

(51) Int. Cl.
*A61K 31/438* (2006.01)
*C07D 215/02* (2006.01)
(52) U.S. Cl. ......................................... 514/278; 546/16
(58) Field of Classification Search .................. None
See application file for complete search history.

(56) References Cited

FOREIGN PATENT DOCUMENTS

| WO | WO 03/033476 A1 | 4/2003 |
|---|---|---|
| WO | WO 03/033480 A1 | 4/2003 |
| WO | WO 03/097047 A1 | 11/2003 |
| WO | WO 2004/011438 A1 | 2/2004 |
| WO | WO 2004/024702 A1 | 3/2004 |
| WO | WO 2005/040157 A2 | 5/2005 |
| WO | WO 2005/070898 A1 | 8/2005 |
| WO | WO 2005/070925 A1 | 8/2005 |
| WO | WO 2005/085200 A1 | 9/2005 |
| WO | WO 2005/103039 A1 | 11/2005 |
| WO | WO 2006/018280 A2 | 2/2006 |

OTHER PUBLICATIONS

Bittencourt, J., et al. "The Melanin-Concentrating Hormone System of the Rat Brain: An Immuno- and Hybridization Histochemical Characterization", the Journal of Comparative Neurology 319:218-245 (1992).
Borowsky, B., et al. "Antidepressant, Anxiolytic and Anorectic Effects of a Melanin-Concentrating Hormone-1 Receptor Antagonist", Nature Medicine vol. 8, No. 8, (2002), p. 825.
Chaki, S., et al. "MGS0039: A Potent and Selective Group II Metabotropic Glutamate Receptor Antagonist with Antidepressant-Like Activity:" Neuropharmacology 46 (2004) p. 457-467.
Dyke, H., et al. "Recent Developments in the Discovery of MCH-'1R Antagonists for the Treatment of Obesity-an Update", Expert Opinion Ther. Patents (2005), 15(10), p. 1303-1313.
Hervieu, G., et al. "The Distribution of the mRNA and Protein Products of the Melanin-Concentrating Hormone (MCH) Receptor Gene, sic-1, in the Central Nervous System of the Rat", European Journal of Neuroscience, vol. 12, pp. 1194-1215 (2000).
Kennedy, A., et al. "Effect of Direct Injection of Melanin-Concentrating Hormone into the Paraventricular Nucleus: Further Evidence for a Stimulatory Role in the Adrenal Axis via SLC-1", Journal of Neuroendocrinology vol. 15, p. 268-272 2003).
Qu, D., et al. "A Role for Melanin-Concentrating Hormone in the Central Regulation of Feeding Behaviour", Letters to Nature, vol. 380 p. 243 (1996).
Saito, Y., et al. "Expression of the Melanin-Concentrating Hormone (MCH) Receptor mRNA in the Rat Brain", Journal of Comparative Neurology 435:26 (2001).
Stella, V., et al. "Prodrugs: Do They Have Advantages in Clinical Practice", Drugs 29: 455-473 (1985).
Stella, V., "Prodrugs: The Control of Drug Delivery via Bioreversible Chemical Modification", Drug Delivery Systems p. 112-176 (1985).
Tan, C., et al. "Melanin-Concentrating Hormone Receptor Subtypes 1 and 2: Species-Specific Gene Expression", Genomics vol. 79, No. 6 p. 785 (2002).
Verret, L., et al. "A Role of Melanin-Concentrating Hormone Producing Neurons in the Central Regulation of Paradoxical Sleep", MBC Neuroscience, 4:19 p. 1-10 (2003).

*Primary Examiner* — Kamal Saeed
(74) *Attorney, Agent, or Firm* — Peter Herridge

(57) ABSTRACT

The present invention concerns aryl and heteroaryl substituted diaza-spiro-pyridinone derivatives having antagonistic melanin-concentrating hormone (MCH) activity, in particular MCH-1 activity according to the general Formula (I)

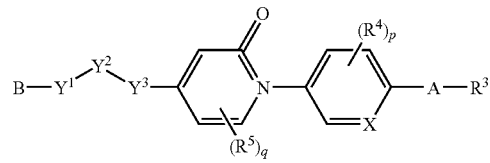

(I)

a pharmaceutically acceptable acid or base addition salt thereof, an N-oxide form thereof or a quaternary ammonium salt thereof, wherein the variables are defined in Claim 1. It further relates to their preparation, compositions comprising them and their use as a medicine. The compounds according to the invention are useful for the prevention and/or treatment of psychiatric disorders, including but not limited to anxiety, eating disorders, mood disorders, such as bipolar disorders and depression, psychoses, such as schizophrenia, and sleeping disorders; obesity; diabetes; sexual disorders and neurological disorders.

23 Claims, No Drawings

SUBSTITUTED DIAZA-SPIRO-PYRIDINONE DERIVATIVES FOR USE IN MCH-1 MEDIATED DISEASES

CROSS REFERENCE TO RELATED APPLICATIONS

This application claims priority of the benefits of the filing of patent application Nos. EP06125421.5 filed Dec. 5, 2006, and PCT/EP2007/063310 filed Dec. 4, 2007. The disclosures of the aforementioned related patent applications are hereby incorporated herein by reference for all purposes.

CROSS-REFERENCE TO RELATED APPLICATIONS

This application claims priority to the benefits of the filing of Application Nos. EP 06125421.5 filed Dec. 5, 2006, and PCT/EP2007/063310 filed Dec. 4, 2007. The complete disclosures of the aforementioned related patent applications are hereby incorporated herein by reference for all purposes.

FIELD OF THE INVENTION

The present invention concerns aryl and heteroaryl substituted diaza-spiro-pyridinone derivatives having antagonistic melanin-concentrating hormone (MCH) activity, in particular MCH-1 activity. It further relates to their preparation, compositions comprising them and their use as a medicine.

BACKGROUND OF THE INVENTION

Melanin concentrating hormone (MCH) is a cyclic 19-amino acid polypeptide, which is mainly produced by hypothalamic neurons projecting widely throughout the central nervous system (CNS) (J. Comp. Neurol. (1992) 319, 218-245). MCH mediates its effects through two G protein-coupled receptors (GPCRS) termed MCH-1 and MCH-2 (reviewed in Doggrell, 2003). While in rodents only the MCH-1 receptor is expressed, human and primates express both MCH-1 and MCH-2 receptors (Genomics (2002), 79, 785-792). Originally, the MCH-1 receptor was considered a valuable target for the treatment of obesity as MCH promotes feeding behaviour in rodents (Nature (1996), 380, 243-247). Recently however, it was shown that MCH-1 antagonism produces anxiolytic and antidepressant profiles in rodents (Nat. Med. (2002) 8, 825-830; Neuropharmacology (2004), 46, 457-467; Neuropsychopharmacology (2006), 31(1), 112-120; Neuropsychopharmacology (2006), 31(6), 1135-1145). Thus, it is currently generally accepted that MCH receptors, particularly the MCH-1 receptor, are a good target for the treatment of affective spectrum disorders (Eur. J. Neuroscience (2000) 12, 1194-1216).

MCH-1 receptor mRNA and protein are distributed in various hypothalamic nuclei including the paraventricular nucleus and several limbic structures all implicated in the regulation of emotion and stress (Eur. J. Neuroscience (2000) 12, 1194-1216). In addition, dense labelling is detected in the nucleus accumbens shell (J. Comp. Neurol. (2001) 435, 26-40). Injection of MCH directly into the paraventricular nucleus has been found to increase plasma adrenocorticotropic hormone (ACTH) and to alter sleep architecture (Verret et al. 2003, BMC Neurosci 4:19). MCH also induces corticotrophin-releasing factor (CRF) release from hypothalamic explants, an effect that is sensitive to blockade by an MCH-1 receptor antagonist (J. Neuroendrocrinol. (2003) 15, 268-2729). Thus it seems likely that stimulation of MCH-1 receptor causes activation of the hypothalamus-pituitary-adrenal (HPA) axis through increases in CRF release. Injection of MCH into the nucleus accumbens shell, in which MCH-1 receptor is abundant, increased immobility in a forced swim test in rats, suggesting increased depressive behaviour (Soc. Neurosci. Abstr. (2004) 763.9). Moreover, Borowsky et al. (Nat. Med. (2002) 8, 825-830) reported the MCH-1 antagonist, SNAP-7941, exhibited antidepressant- and axiolytic-like affects in rodents tests, supporting a role for MCH-1 receptor in depression and anxiety.

BACKGROUND PRIOR ART

A large number of companies is now actively pursuing the development of MCH-1 antagonists and a wide range of structural types have been reported in a number of patent publications, mostly in relation to the regulation of food intake and energy expenditure (Expert Opin. Ther. Patents (2005) 15(10)). The majority of reported MCH-antagonists incorporate a basic centre and two (hetero)aromatic parts, joined by linkers. WO 2005/085200 (Banyu Pharmaceutical Co., Ltd) discloses pyridinone, pyrimidinone and pyridazinone-derivatives for use as MCH-1 antagonists. WO 2003/033480, WO 2003/033476 and WO 2005/05042541 (Glaxo Group Limited), WO 2004/024702 (Boehringer Ingelheim Pharma GMBH & Co. KG) and WO 2005/103039 (Neurocrine Biosciences Inc.) disclose different bicyclic heterocycles, such as thieno-pyrimid-4-one-, benzopyrimid-4-one- and phtalimide-derivatives, for use as MCH-1 antagonists. WO 2003/097047 and WO 2005/040157 (Eli Lilly and Company) and WO 2005/070925 (Aventis Pharma Deutschland GmbH) report different aromatic 5-membered ring heterocycles, such as oxazole- and oxadiazole-derivatives, for use as MCH-1 antagonists. WO 2004/011438 and WO 2005/070898 (Aventis Pharma Deutschland GMBH) disclose diaryl-substituted cyclic urea derivatives as MCH-1 antagonist.

DESCRIPTION OF THE INVENTION

It is an object of the present invention to provide a compound with a binding affinity towards melanin-concentrating (MCH) receptors, in particular towards MCH-1 receptors, in particular as an antagonist.

Moreover, it has been found that the compounds according to the invention exhibit very low or no hERG-channel interactions, which interactions are undesirable, but widely associated with the compounds of the prior art. Hence, the compounds of the invention are preferred over the prior art compounds for their substantial lack of hERG-channel interactions and their absence of QT-prolongation.

This goal was achieved by a novel substituted diaza-spiro-pyridinone derivative according to the general Formula (I)

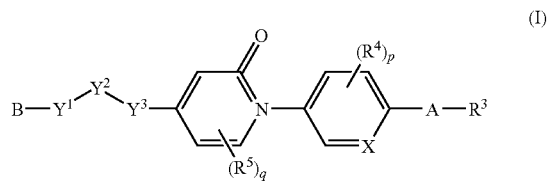

a pharmaceutically acceptable acid or base addition salt thereof, an N-oxide form thereof or a quaternary ammonium salt thereof, wherein:

A is a radical according to Formula (II)

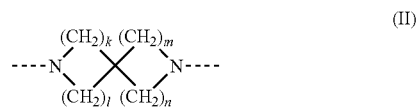

wherein
k, l, m, n are each independently from each other, an integer equal to 0, 1, 2, 3, or 4, with the provision that (k+1) and (m+n) is equal to 2, 3, 4, or 5; wherein one of the —CH$_2$— moieties may be replaced by O; and wherein each of the—CH$_2$— moieties may be substituted with oxo X is C or N;

R$^3$ is selected from the group of hydrogen, C$_{1-5}$alkyl, C$_{3-6}$cycloalkyl, and C$_{1-5}$alkyloxycarbonyl;

R$^4$, R$^5$ are each, independently from each other, selected from the group of hydrogen, halo, cyano, hydroxy, amino, oxo, carboxyl, nitro, thio, formyl, C$_{1-3}$alkyl, and C$_{1-3}$alkyloxy;

p is an integer, equal to zero, 1, 2, or 3 q is an integer, equal to zero, 1, 2, or 3

Y$^1$, Y$^3$ are each, independently from each other, selected from the group of a single bond, O, NR$^7$, S, SO, and SO$_2$; wherein R$^7$ is selected from the group of hydrogen and C$_{1-3}$alkyl;

Y$^2$ is a saturated or unsaturated, straight or branched C$_{1-6}$-hydrocarbon radical, wherein one or more hydrogen atoms may optionally be replaced by a radical selected from the group of halo, cyano, hydroxy, amino, oxo, carboxyl, nitro, thio, and formyl;

B is a 6-membered ring containing zero, 1, 2 or 3 nitrogen atoms, optionally substituted with r substituents R$^6$, each independently from each other, selected from the group of hydrogen, halo, cyano, hydroxy, amino, oxo, carboxyl, nitro, thio, formyl, C$_{1-3}$alkyl, and C$_{1-3}$alkyloxy; and wherein r is an integer, equal to zero, 1 or 2; or two substituents R$^6$ may be combined into a radical —CH$_2$CH$_2$CH$_2$— or —OCH$_2$O—;

alkyl is a straight or branched saturated hydrocarbon radical having the indicated number of carbon atoms; wherein the radical may optionally be substituted on one or more carbon atoms with one or more radicals selected from the group of halo, cyano, hydroxy, amino, oxo, carboxyl, nitro, thio, and formyl;

aryl is naphthyl or phenyl, each optionally substituted with 1, 2 or 3 substituents, each independently from each other selected from the group of halo, cyano, hydroxy, amino, oxo, carboxyl, nitro, thio, formyl, C$_{1-3}$alkyl, and C$_{1-3}$alkyloxy;

halo is fluoro, chloro, bromo or iodo.

In the framework of this application, with "compounds according to the invention" is meant a compound according to the general Formula (I), a pharmaceutically acceptable acid or base addition salt thereof, an N-oxide form thereof or a quaternary ammonium salt thereof.

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, an N-oxide form thereof, or a quaternary ammonium salt thereof.

The invention also relates to a method for preventing and/or treating a disorder or disease responsive to antagonism of the MCH receptor, in particular to antagonism of the MCH-1 receptor in an individual in need thereof comprising the step of administering to said individual a compound or a pharmaceutical composition according to the present invention. In an embodiment, said disorder or disease is selected from the group comprising psychiatric disorders, including but not limited to anxiety, eating disorders, mood disorders, such as bipolar disorders and depression, psychoses, such as schizophrenia, and sleeping disorders; obesity; diabetes; sexual disorders; and neurological disorders.

The invention also relates to the use of a compound according to the invention as a medicament and for the preparation of a medicament for the prevention and/or treatment of a disorder or disease responsive to antagonism of the MCH receptor, in particular to antagonism of the MCH-1 receptor.

In particular, the invention relates to the use of a compound according to the invention for the preparation of a medicament for the prevention and/or treatment of psychiatric disorders, including but not limited to anxiety, eating disorders, mood disorders, such as bipolar disorders and depression, psychoses, such as schizophrenia, and sleeping disorders. Also, the compound can be used for treating obesity, diabetes, sexual disorders and neurological disorders.

A compound according to the invention, in particular according to Formula (I), may also be suitable as add-on treatment or combination treatment and/or prophylaxis in the above listed diseases, in particular for the prevention and/or treatment of psychiatric disorders, in combination with antidepressants, anxiolytics and/or antipsychotics which are currently available or in development or which will become available in the future, in particular to improve efficacy and/or onset of action. This is evaluated in rodent models in which antidepressants, anxiolytics and/or antipsychotics are shown to be active. For example, compounds are evaluated in combination with antidepressants, anxiolytics and/or antipsychotics for attenuation of stress-induced hyperthermia.

The invention therefore also relates to the use of the compounds according to the invention in combination with one or more other compounds selected from the group of antidepressants, anxiolytics and antipsychotics, to a pharmaceutical composition comprising the compounds according to the invention and one or more other compounds selected from the group of antidepressants, anxiolytics and antipsychotics, as well as to a process for the preparation of such pharmaceutical compositions.

The invention also relates to the use of the compounds according to the invention in combination with one or more other compounds selected from the group of lipid-lowering compounds for the prevention and/or treatment of obesity, to a pharmaceutical composition comprising the compounds according to the invention and one or more other compounds selected from the group of lipid-lowering compounds, as well as to a process for the preparation of such pharmaceutical compositions.

DETAILED DESCRIPTION OF THE INVENTION

In one embodiment, the invention relates to a compound according to the invention, wherein k, l, m, n are each independently from each other, an integer equal to 1, 2, or 3, with the provision that (k+1) and (m+n) is equal to 2, 3, or 4.

In one embodiment, the invention relates to a compound according to the invention, wherein A is selected from the group of radicals (a-1), (a-2), (a-3), (a-4), (a-5), (a-6), (a-7), (a-8), (b-1), (b-2), (b-3), (b-4), (b-5), (b-6), (b-7), (b-8), (b-9), (b-10), (c-1), (c-2), (c-3), (c-4), (c-5), (c-6), (c-7), (c-8), (d-1), (d-2), (d-3), (d-4), (d-5), (d-6), (c-1), (e-2), (e-3), (e-4), (e-5), (e-6), (f-1), (f-2), (f-3), and (f-4), as depicted below, wherein one of the —CH$_2$— moieties may be replaced by O; and wherein each of the —CH$_2$— moieties may be substituted with oxo.
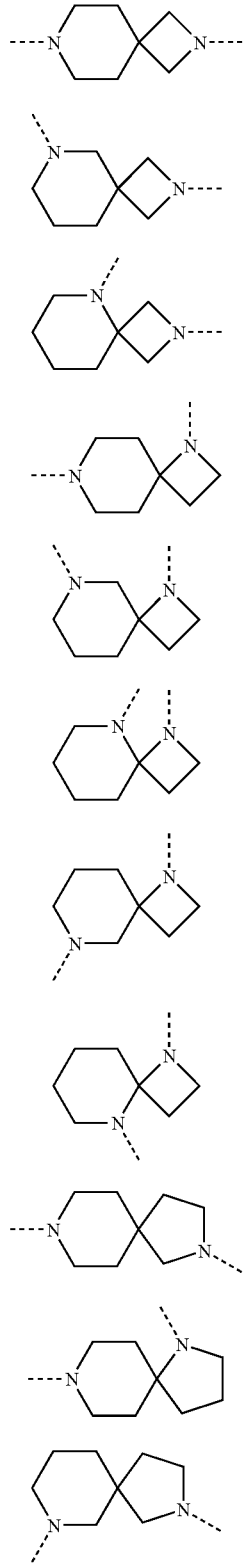
(a-1)
(a-2)
(a-3)
(a-4)
(a-5)
(a-6)
(a-7)
(a-8)
(b-1)
(b-2)
(b-3)
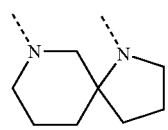
(b-4)
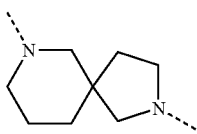
(b-5)
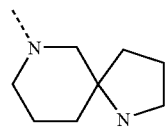
(b-6)
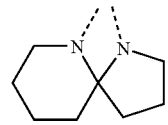
(b-7)
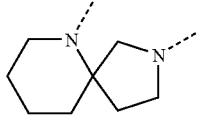
(b-8)
(c-1)
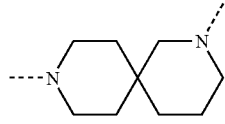
(c-2)
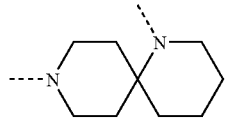
(c-3)
(c-4)
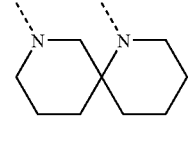
(c-5)
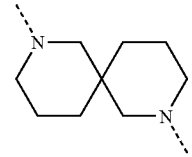
(c-6)

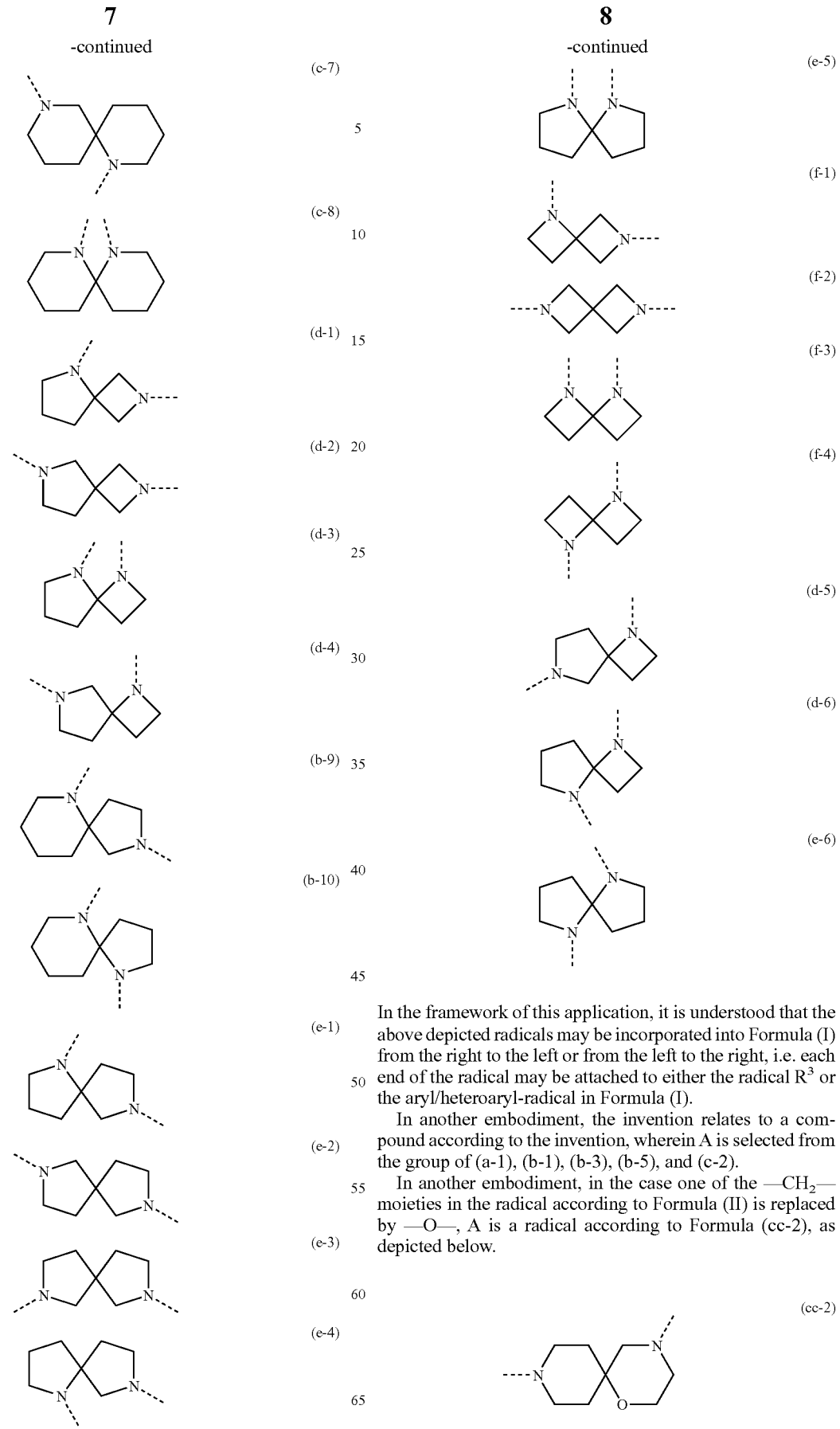

In the framework of this application, it is understood that the above depicted radicals may be incorporated into Formula (I) from the right to the left or from the left to the right, i.e. each end of the radical may be attached to either the radical $R^3$ or the aryl/heteroaryl-radical in Formula (I).

In another embodiment, the invention relates to a compound according to the invention, wherein A is selected from the group of (a-1), (b-1), (b-3), (b-5), and (c-2).

In another embodiment, in the case one of the —$CH_2$— moieties in the radical according to Formula (II) is replaced by —O—, A is a radical according to Formula (cc-2), as depicted below.

In another embodiment, when one of the —CH$_2$— moieties in the radical according to Formula (II) is substituted with oxo, A is a radical according to (aa-1) or (bb-1), as depicted below.

(aa-1)

(bb-1)

In another embodiment, the invention relates to a compound according to the invention, wherein R$^3$ is selected from the group of hydrogen, C$_{3-6}$cycloalkyl and C$_{1-5}$alkyl, in particular from the group of hydrogen C$_{3-5}$cycloalkyl and C$_{1-3}$alkyl, in particular from the group of hydrogen, methyl, ethyl, propyl and cyclopropyl.

In another embodiment, the invention relates to a compound according to the invention, wherein X is carbon or nitrogen.

In another embodiment, the invention relates to a compound according to the invention, wherein each of R$^4$ and R$^5$ independently from each other, are selected from the group of hydrogen, halo, C$_{1-3}$alkyl, and C$_{1-3}$alkyloxy.

In another embodiment, the invention relates to a compound according to the invention, wherein p is zero or 1.

In another embodiment, the invention relates to a compound according to the invention, wherein q is zero.

In another embodiment, the invention relates to a compound according to the invention, wherein Y$^1$ and Y$^3$ are each, independently from each other, selected from the group of a single bond and O.

In another embodiment, the invention relates to a compound according to the invention, wherein Y$^2$ is selected from the group of —CH$_2$—, —CH$_2$CH$_2$—, and —CH=CH—.

In another embodiment, the invention relates to a compound according to the invention, wherein B is selected from the group of phenyl, pyridinyl, pyridazinyl, pyrimidinyl, pyrazinyl, and triazinyl; in particular from the group of phenyl, pyridinyl and pyridazinyl; in particular is B phenyl.

In another embodiment, the invention relates to a compound according to the invention, wherein B is substituted with one halo substituent, in particular fluoro or halo.

In another embodiment, the invention relates to a compound according to the invention, wherein the moiety B—Y$^1$—Y$^2$—Y$^3$ is selected from the radicals (a1-1) to (d1-5) as listed below, optionally substituted with r substituents R$^6$, each independently from each other, selected from the group of halo, cyano, hydroxy, amino, oxo, carboxyl, nitro, thio, formyl, C$_{1-3}$alkyl, and C$_{1-3}$alkyloxy; and wherein r is an integer, equal to 1 or 2; or two substituents R$^6$ may be combined into a radical —CH$_2$CH$_2$CH$_2$— or —OCH$_2$O—.

(a1-1)

(a1-2)

(a1-3)

(a1-4)

(a1-5)

(b1-1)

(b1-2)

(b1-3)

(b1-4)

(b1-5)

(c1-1)

(c1-2)

-continued

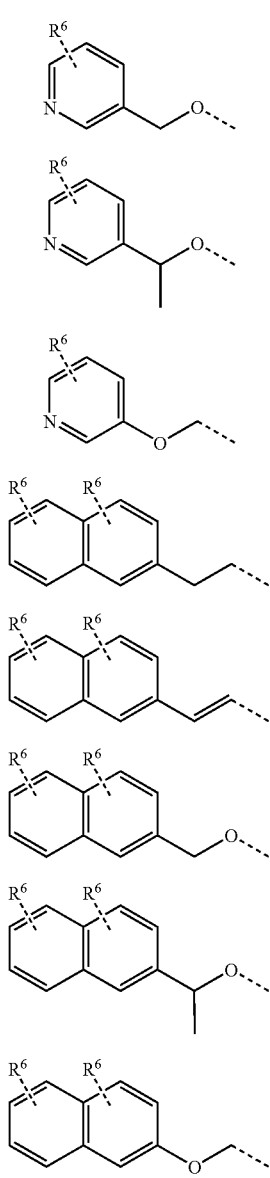

(c1-3)
(c1-4)
(c1-5)
(d1-1)
(d1-2)
(d1-3)
(d1-4)
(d1-5)

In another embodiment, the moiety B—Y$^1$—Y$^2$—Y$^3$ is selected from the radicals (a1-2), (a1-3) and (a1-5), optionally substituted with r substituents R$^6$, each independently from each other, selected from the group of halo, cyano, hydroxy, amino, oxo, carboxyl, nitro, thio, formyl, C$_{1-3}$alkyl, and C$_{1-3}$alkyloxy; and wherein r is an integer, equal to 1 or 2; or two substituents R$^6$ may be combined into a radical —CH$_2$CH$_2$CH$_2$— or —OCH$_2$O—.

In a further embodiment, the invention relates to a compound according to the invention, wherein one or more, in combination or alone, of the following restrictions apply:

k, l, m, n are each independently from each other, an integer equal to 1, 2, or 3, with the provision that (k+l) and (m+n) is equal to 2, 3, or 4;

A is selected from the group of radicals (a-1), (a-2), (a-3), (a-4), (a-5), (a-6), (a-7), (a-8), (a-9), (a-10), (a-11), (b-1), (b-2), (b-3), (b-4), (b-5), (b-6), (b-7), (b-8), (b-9), (b-10), (c-1), (c-2), (c-3), (c-4), (c-5), (c-6), (c-7), (c-8), (d-1), (d-2), (d-3), (d-4), (d-5), (d-6), (e-1), (e-2), (e-3), (e-4), (e-5), (e-6), (f-1), (f-2), (f-3), and (f-4), wherein one of the —CH$_2$— moieties may be replaced by O; and wherein each of the —CH$_2$— moieties may be substituted with oxo; or A is selected from the group of (a-1), (b-1), (b-3), (b-5), and (c-2); or A is a radical according to Formula (cc-2); or A is a radical according to (aa-1) or (bb-1);

R$^3$ is selected from the group of hydrogen, C$_{3-6}$cycloalkyl, and C$_{1-5}$alkyl, in particular from the group of hydrogen, C$_{3-6}$cycloalkyl, and C$_{1-3}$alkyl, in particular from the group of hydrogen, methyl, ethyl, propyl and cyclopropyl;

X is carbon;

each of R$^4$ and R$^5$, independently from each other, are selected from the group of hydrogen, halo, C$_{1-3}$alkyl, and C$_{1-3}$alkyloxy;

p is zero or;

q is zero;

Y$^1$ and Y$^3$ are each, independently from each other, selected from the group of a single bond and O;

Y$^2$ is selected from the group of —CH$_2$—, —CH$_2$CH$_2$—, and —CH═CH—;

B is selected from the group of phenyl, pyridinyl, pyridazinyl, pyrimidinyl, pyrazinyl, and triazinyl; in particular from the group of phenyl, pyridinyl and pyridazinyl; in particular is B phenyl;

B is substituted with one halo substituent, in particular fluoro or halo;

B—Y$^1$—Y$^2$—Y$^3$ is selected from the radicals (a1-1) to (d1-5), optionally substituted with r substituents R$^6$, each independently from each other, selected from the group of halo, cyano, hydroxy, amino, oxo, carboxyl, nitro, thio, formyl, C$_{1-3}$alkyl, and C$_{1-3}$alkyloxy; and wherein r is an integer, equal to 1 or 2; or two substituents R$^6$ may be combined into a radical —CH$_2$CH$_2$CH$_2$— or —OCH$_2$O—; or B—Y$^1$—Y$^2$—Y$^3$ is selected from the radicals (a1-2), (a1-3) and (a1-5), optionally substituted with r substituents R$^6$, each independently from each other, selected from the group of halo, cyano, hydroxy, amino, oxo, carboxyl, nitro, thio, formyl, C$_{1-3}$alkyl, and C$_{1-3}$alkyloxy; and wherein r is an integer, equal to 1 or 2; or two substituents R$^6$ may be combined into a radical —CH$_2$CH$_2$CH$_2$— or —OCH$_2$O—.

In another embodiment, the invention relates to a compound according to the invention, wherein A is selected from the group of (a-1), (b-1), (b-3), (b-5), and (c-2),

(a-1)

(b-1)

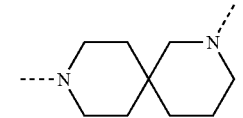

(c-1)

X is C or N;
R³ is selected from the group of hydrogen, C₃₋₆cycloalkyl, and C₁₋₅alkyl;
R⁴, R⁵ are each, independently from each other, selected from the group of hydrogen, halo, C₁₋₃alkyl, and C₁₋₃alkyloxy;
p is an integer, equal to zero, or 1;
q is an integer, equal to zero;
the moiety B—Y¹—Y²—Y³ is selected from the radicals (a1-2), (a1-3) and (a1-5), optionally substituted with r substituents R⁶

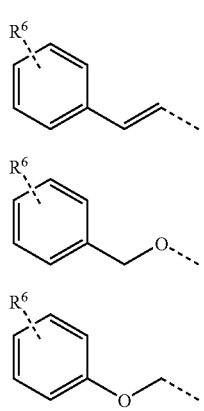

(a1-2)

(a1-3)

(a1-5)

R⁶ is a halo substituent; and wherein r is an integer, equal to 1 or 2.

In another embodiment, the invention relates to a compound according to the invention, wherein
A is selected from the group of (a-1), (b-1), (b-3), (b-5), and (c-2),

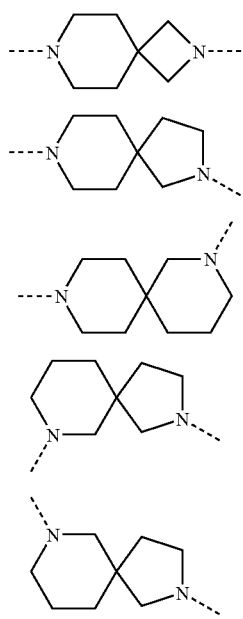

(a-1)

(b-1)

(c-2)

(b-3)

(b-5)

X is C or N;
R³ is selected from the group of hydrogen, C₃₋₅cycloalkyl, and C₁₋₃alkyl;
R⁴, R⁵ are each, independently from each other, selected from the group of hydrogen, halo, C₁₋₃alkyl, and C₁₋₃alkyloxy;

p is an integer, equal to zero, or 1;
q is an integer, equal to zero;
Y¹, Y³ are each, independently from each other, selected from the group of a single bond or O;
Y² is a saturated or unsaturated, straight or branched C₁₋₆-hydrocarbon radical; and
B is phenyl, optionally substituted with one halo substituent R⁶.

In another embodiment, the invention relates to a compound according to the invention, wherein
A is selected from the group of (a-1), or (b-1);

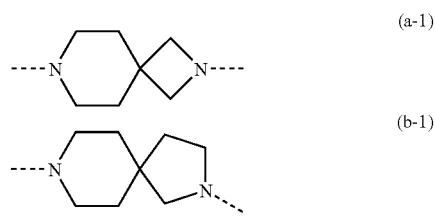

(a-1)

(b-1)

X is C;
R³ is a methyl;
R⁴, R⁵ are each, independently from each other, selected from the group of hydrogen, or halo;
p is an integer, equal to zero, or 1;
q is an integer, equal to zero;
Y¹ is a single bond;
Y³ is O;
Y² is a CH₂; and
B is phenyl.

In the framework of this application, alkyl is a straight or branched saturated hydrocarbon radical having the indicated number of carbon atoms, i.e. when C₁₋₃alkyl is indicated, the alkyl radical may contain from 1 to 3 carbon atom; or when C₁₋₅alkyl is indicated, the alkyl radical may contain from 1 to 5 carbon atom. Each radical may optionally be substituted on one or more carbon atoms with one or more substituents selected from the group of halo, cyano, hydroxy, amino, oxo, carboxyl, nitro, thio, and formyl. Preferably, alkyl is methyl, ethyl, propyl or isopropyl. Further radicals that are embraced within the scope are e.g. hydroxymethyl, 1-hydroxyethyl, 1-hydroxypropyl, fluoromethyl, difluoromethyl and trifluoromethyl.

In the framework of this application, C₃₋₆cycloalkyl as a group or part of a group defines cyclic saturated hydrocarbon radicals having from 3 to 6 carbon atoms such as cyclopropyl, cyclobutyl, cyclopentyl or cyclohexyl. C₃₋₆cycloalkyl may optionally be substituted on one or more carbon atoms with one or more substituents selected from the group of halo, cyano, hydroxy, amino, oxo, carboxyl, nitro, thio, and formyl.

In the framework of this application, aryl is naphthyl or phenyl, each optionally substituted with 1, 2 or 3 substituents, each independently from each other, selected from the group of halo, cyano, hydroxy, amino, oxo, carboxyl, nitro, thio, formyl, and C₁₋₃alkyloxy.

In the framework of this application, halo is a substituent selected from the group of fluoro, chloro, bromo, and iodo. Preferably, halo is fluoro, chloro or bromo.

In the framework of this application, unless otherwise indicated, a bond can be any bond, including a covalent bond, a single bond, a double bond, a triple bond, a coordination bond, and a hydrogen bond.

A pharmaceutically acceptable acid addition salt is defined to comprise a therapeutically active non-toxic acid addition salt form that a compound according to Formula (I) is able to form. Said salt can be obtained by treating the base form of a compound according to Formula (I) with an appropriate acid, for example an inorganic acid, for example hydrohalic acid, in particular hydrochloric acid, hydrobromic acid, sulphuric acid, nitric acid and phosphoric acid; an organic acid, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said acid addition salt form may be converted into the free base form by treatment with an appropriate base.

The compound according to Formula (I) containing an acidic proton may also be converted into a therapeutically active non-toxic metal or amine addition salt form (base addition salt) by treatment with an appropriate organic and inorganic base. Appropriate base salt forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salt form can be converted into the free form by treatment with an appropriate acid.

The term addition salt as used in the framework of this application also comprises a solvate that the compound according to Formula (I), as well as a salt thereof, is able to form. Such solvates are, for example, hydrates and alcoholates.

The N-oxide form of the compound according to Formula (I) is meant to comprise a compound of Formula (I) wherein one or several nitrogen atoms are oxidized to so-called N-oxides, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for a compound according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

A compound of Formula (I) may be converted to the corresponding N-oxide form following art-known procedures for converting a trivalent nitrogen into its N-oxide form. Said N-oxidation reaction may generally be carried out by reacting the compound of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A quaternary ammonium salt of compound according to Formula (I) defines said compound which is able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has at least one positively charged nitrogen. Pharmaceutically acceptable counterions include chloro, bromo, iodo, trifluoroacetate and acetate ions.

The invention also comprises a derivative compound (usually called "pro-drug") of a pharmacologically-active compound according to the invention, in particular according to Formula (I), which is degraded in vivo to yield a compound according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

A pro-drug form of a pharmacologically-active compound according to the invention will generally be a compound according to Formula (I), a pharmaceutically acceptable acid or base addition salt thereof, an N-oxide form thereof, or a quaternary ammonium salt thereof, having an acid group which is esterified or amidated. Included in such esterified acid groups are groups of the formula —COOR$^x$, where R$^x$ is a C$_{1-6}$alkyl, phenyl, benzyl or one of the following groups:

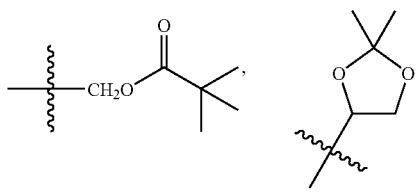

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl. A compound according to the invention having an amino group may be derivatised with a ketone or an aldehyde such as formaldehyde to form a Mannich base. This base will hydrolyze with first order kinetics in aqueous solution.

In the framework of this application, a compound according to the invention is inherently intended to comprise all stereochemically isomeric forms thereof. The term "stereochemically isomeric form" as used herein defines all the possible stereochemically isomeric forms that a compound of Formula (I) may possess. Unless otherwise mentioned or indicated, the chemical designation of a compound denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Hence, all stereochemically isomeric forms of a compound of Formula (I) are intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in a compound according to Formula (I)) relative to the position of the highest priority substituent on the reference atom is denominated "α", if it is on the same side of the mean plane determined by the ring system, or "β", if it is on the other side of the mean plane determined by the ring system.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{13}O$ and mixtures thereof; and when fluor is mentioned, it is understood to refer to $^{18}F$, $^{19}F$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), a pharmaceutically acceptable acid or base addition salt thereof, an N-oxide form thereof, or a quaternary ammonium salt thereof, which contains at least one radioactive atom. For example, a compound can be labelled with positron or with gamma emitting radioactive isotopes. For radioligand-binding techniques (membrane receptor assay), the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen, and halogen. Preferably, the radioactive atom is selected from the group of hydrogen, carbon, and halogen.

In particular, the radioactive isotope is selected from the group of $^3H$, $^{11}C$, $^{18}F$, $122I$, $^{123}I$, $^{125}I$, $^{131}I$, $^{75}Br$, $^{76}Br$, $^{77}Br$, and $^{82}Br$. Preferably, the radioactive isotope is selected from the group of $^3H$, $^{11}C$, and $^{18}F$.

Preparation

A compound according to the invention can generally be prepared by a succession of steps, each of which is known to the skilled person. In particular, a pyridinone derivative can be prepared according to one or more of the following preparation methods.

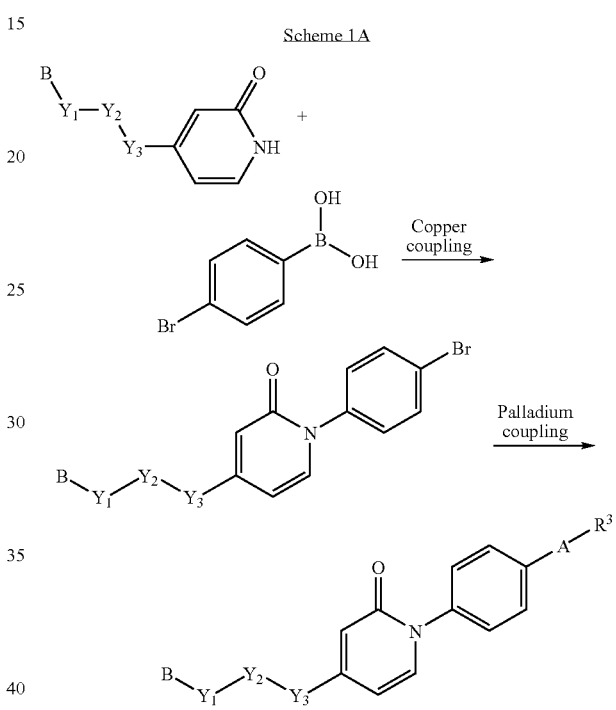

Scheme 1A

The copper coupling reaction is performed in the presence of a copper salt, such as $Cu(OAc)_2$, in an aprotic solvent such as DCE, in the presence of an amine or amine N-oxide, such as pyridine or NMO, at a convenient temperature, either by conventional heating or under microwave irradiation, for a period of time to ensure the completion of the reaction, typically 15 min at 180° C. under microwave irradiation. The palladium coupling reaction is performed in an aprotic solvent such as toluene, in the presence of a palladium catalyst such as $Pd(AcO)_2$, and in the presence of tBuOK, as a base, and a ligand, such as BINAP, at a convenient temperature, either by conventional heating or under microwave irradiation, for a period of time to ensure the completion of the reaction, typically 24 hours at 100° C. under traditional heating.

When A-$R^3$ is an amide the coupling reaction is performed in an aprotic solvent such as dioxane or DMF, in the presence of CuI, N,N-dimethylethylendiamine and $K_3PO_4$ as a base, at a convenient temperature, either by conventional heating or under microwave irradiation, for a period of time to ensure the completion of the reaction, typically 20 minutes at 175° C. under microwave irradiation.

When the amino group is protected with a protecting group, deprotection reactions are performed by well known synthetic methods. Transformation of the amino group into different derivatives can be performed by synthetic methods well known to the skilled person.

Also, pyridinone derivative can be prepared according the procedure described in Scheme 1B.

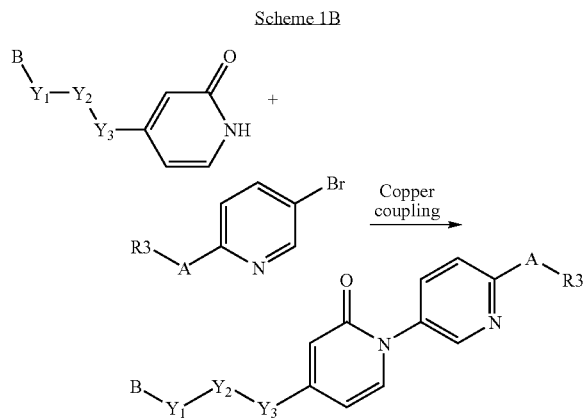

Scheme 1B

The copper coupling reaction is performed in an aprotic solvent such as dioxane or DMF, in the presence of CuI, N,N-dimethylethylendiame as a ligand, and an inorganic base such as $K_3PO_4$, at a convenient temperature, either by conventional heating or under microwave irradiation, for a period of time to ensure the completion of the reaction, typically 20 minutes at 175° C. under microwave irradiation.

Ortho-substituted phenyl derivatives can be prepared according to Scheme 2.

The Hal-radical is a halogen, such as Br, or I. X can be OH, Br or I. The copper coupling reaction is performed in an aprotic solvent such as dioxane or DMF, in the presence of CuI, N,N-dimethylethylenediamine as a ligand, and an inorganic base such as $K_3PO_4$, at a convenient temperature, either by conventional heating or under microwave irradiation, for a period of time to ensure the completion of the reaction, typically 20 minutes at 175° C. under microwave irradiation.

The OH-activation can be done via triflate, in the presence of trifluoromethanesulfonic anhydride or 1,1,1-trifluoro-N-phenyl-N-[(trifluoromethyl)sulfonyl]-methanesulfon-amide, in an aprotic solvent such as DCM or THF, at a convenient temperature for completion of the reaction. The palladium coupling reaction is performed in an aprotic solvent such as toluene or trifluorotoluene in the presence of a palladium catalyst such as $Pd(AcO)_2$, and in the presence of a base, such as tBuOK, or $Cs_2CO_3$, and optionally a ligand, such as BINAP or xantphos is required, at a convenient temperature, either by conventional heating or under microwave irradiation, for a period of time to ensure the completion of the reaction, typically 24 hours at 100° C. under traditional heating.

Compounds according to the invention with substituents other than benzyloxy are prepared according to Scheme 3A, Scheme 3B.

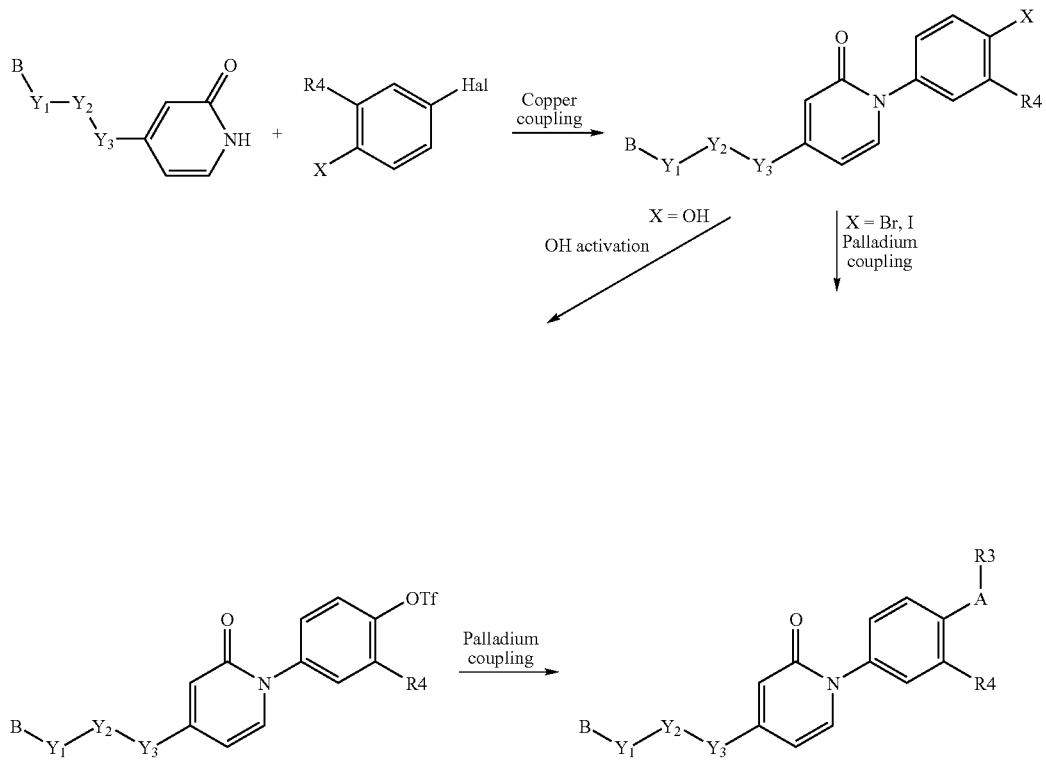

Scheme 2

Scheme 3A

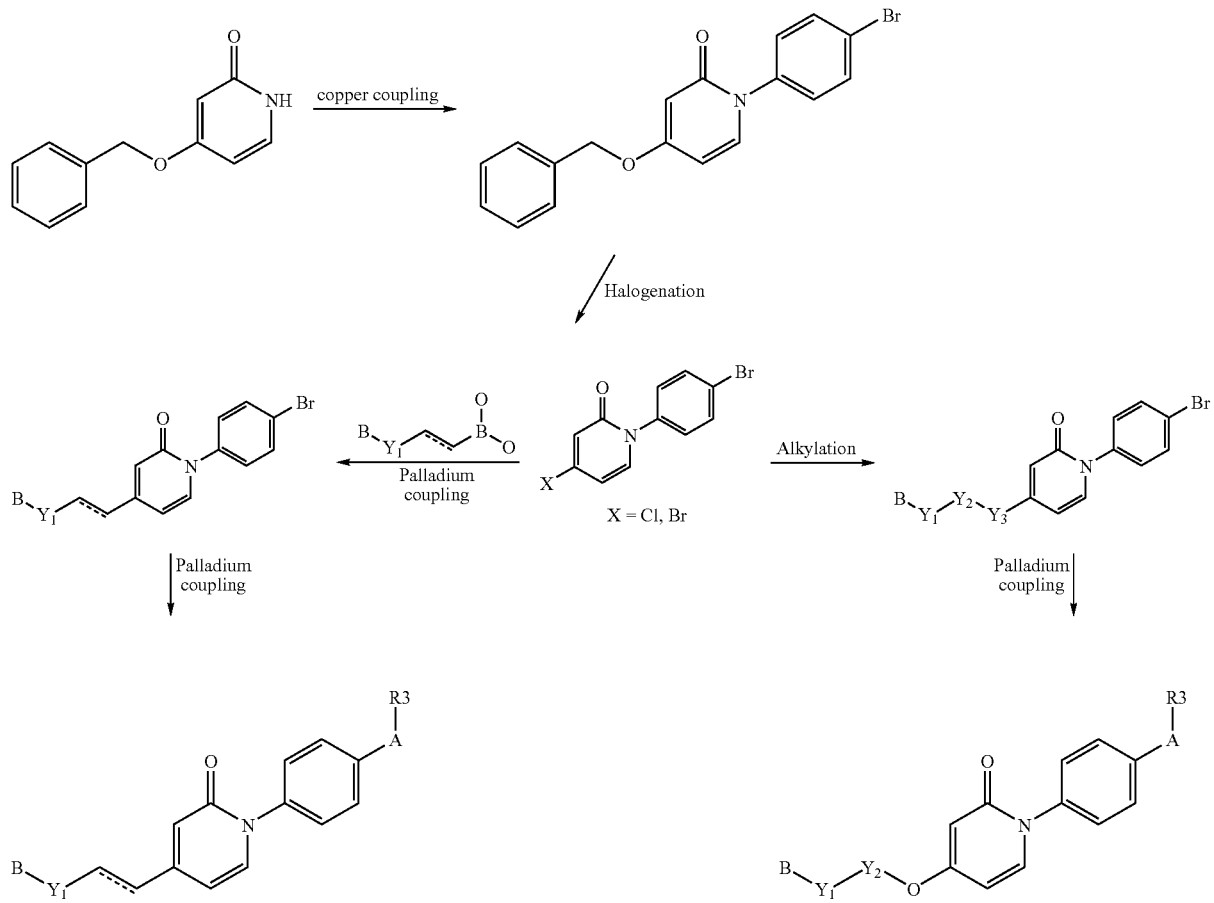

The copper coupling reaction is performed in the presence of a copper salt, such as $Cu(OAc)_2$, in an aprotic solvent such as DCE, in the presence of an amine or amine N-oxide, such as pyridine or NMO, at a convenient temperature, either by conventional heating or under microwave irradiation, for a period of time to ensure the completion of the reaction, typically 15 min at 180° C. under microwave irradiation.

Halogenation is performed in the presence of phosphorus oxybromide or oxychloride, in an aprotic solvent such as DCE, at a convenient temperature to completion of the reaction, typically 150° C. under microwave irradiation.

Alkylation is performed in the presence of an organic or inorganic base, such as NaH, or 1,8-diazabicyclo[5.4.0]undecene-7, in an aprotic solvent such as DME, $CH_3CN$, or DMF at a convenient temperature to completion of the reaction, typically 120° C. for 10 minutes under microwave irradiation. Palladium coupling reaction is performed in an aprotic solvent such as toluene or dioxane in the presence of a palladium catalyst such as $Pd(AcO)_2$, or $Pd(PPh_3)_4$ and in the presence of a base, such as tBuOK, or inorganic aqueous base such as $Na_2CO_3$, and sometimes a ligand, such as BINAP, is required, at a convenient temperature, either by conventional heating or under microwave irradiation, for a period of time to ensure the completion of the reaction, typically 24 hours at 100° C. under traditional heating.

Other compounds were synthesised following Scheme 3B.

Scheme 3B

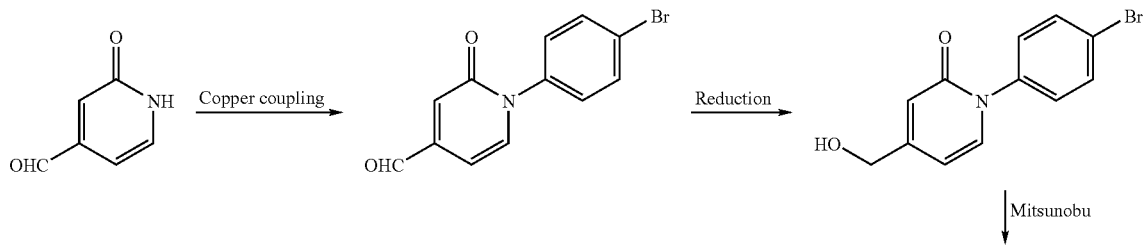

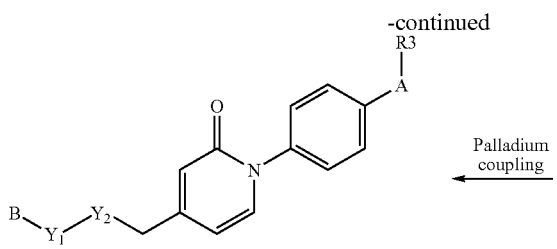 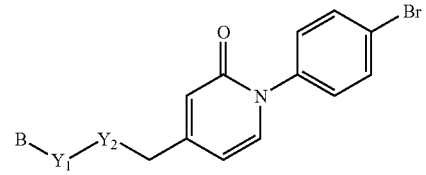

The copper coupling reaction is performed in the presence of a copper salt, such as Cu(OAc)$_2$, in an aprotic solvent such as DCE, in the presence of an amine or amine N-oxide, such as pyridine or NMO, at a convenient temperature, either by conventional heating or under microwave irradiation, for a period of time to ensure the completion of the reaction, typically 15 min at 180° C. under microwave irradiation.

The reduction reaction is performed in a protic solvent such as MeOH and in the presence of a reducing agent such as sodium borohydride, at room temperature and for a period of time to ensure the completion of the reaction, typically 30 min at room temperature.

A Mitsunobu type reaction can be performed in the presence of a phosphine, such as triphenylphosphine, an azodicarboxylate derivative, such as diethylazodicarboxilate in an aprotic solvent, such as THF, at a convenient temperature and for a period of time to ensure the completion of the reaction, such as 100° C. for 5 minutes under microwave irradiation.

The palladium coupling reaction is performed in an aprotic solvent such as toluene, in the presence of a palladium catalyst such as Pd(AcO)$_2$, and in the presence of tBuOK, as a base, and a ligand, such as BINAP, at a convenient temperature, either by conventional heating or under microwave irradiation, for a period of time to ensure the completion of the reaction, typically 24 hours at 100° C. under traditional heating.

Pharmacology

A compound according to the invention, in particular compounds according to Formula (I), the pharmaceutically acceptable acid or base addition salts thereof, an N-oxide form thereof or a quaternary ammonium salt thereof, have surprisingly been shown to have a binding affinity towards the MCH-receptor, in particular towards the MCH-1 receptor, in particular as an antagonist.

In view of their above mentioned potency, a compound according to the invention are suitable for the prevention and/or treatment of diseases where antagonism of the MCH-receptor, in particular antagonism of the MCH-1 receptor is of therapeutic use. In particular, a compound according to the invention may be suitable for treatment and/or prophylaxis of psychiatric disorders, including but not limited to:

anxiety, including but not limited to agoraphobia; generalized anxiety; compulsion; obsessive-compulsive disorder; panic disorder; social phobia; and stress, such a post-traumatic stress;

attention deficit/hyperactivity disorder;

autism;

dysthymia;

eating disorder, including but not limited to anorexia; binge eating; and bulimia nervosa;

impulse control disorder;

mental retardation, including but not limited to fragile X syndrome;

mood disorder, including but not limited to agitation; bipolar disorder, such as bipolar affective disorder, bipolar disorder (I), bipolar disorder (II), hypomania and mania; depression, such as major depression and suicidal depression; seasonal mood disorder; and suicide;

premenstrual syndrome, including but not limited to dysphoria;

psychosis, including but not limited to aggressiveness; drug-induced psychosis; schizoaffective disorder; schizophrenia, such as delusion, catatonia, catatonic schizophrenia, disorganized schizophrenia, paranoid schizophrenia, residual schizophrenia and schizophreniform disorder; and dyssomnia, such as secondary dyssomnia;

sleep disorder, including but not limited to circadian rhythm disorder; hypersomnia; insomnia; narcolepsy and sleep apnea;

stuttering; and violence.

Additionally, a compound according to the invention may be used for treating sexual disorders, neurological disorders, and most in particular obesity and diabetes.

The invention therefore relates to a compound according to the general Formula (I), a pharmaceutically acceptable acid or base addition salt thereof, an N-oxide form thereof or a quaternary ammonium salt thereof, for use as a medicine.

The invention also relates to the use of a compound according to the invention for the preparation of a medicament for the prevention and/or treatment of diseases where antagonism of the MCH-receptor, in particular antagonism of the MCH-1 receptor is of therapeutic use.

The invention also relates to the use of a compound according to the invention for the preparation of a medicament for the prevention and/or treatment of anxiety, eating disorders, mood disorders, such as bipolar disorders and depression, psychoses, such as schizophrenia, and sleeping disorders. Additionally, a compound according to the invention may be used for treating sexual disorders and neurological disorders, and in particular obesity and diabetes.

Combination Treatments

A compound according to the invention, in particular according to Formula (I) may be co-administered as add-on treatment and/or prophylaxis in the above listed diseases.

In particular a compound according to the invention, in particular according to Formula (I) may be co-administered in combination with antidepressants, anxiolytics and/or antipsychotics which are currently available or in development or which will become available in the future, in particular to improve efficacy and/or onset of action. It will be appreciated that a compound according to the present invention and one or more of the other agents may be present as a combined preparation for simultaneous, separate or sequential use for the prevention and/or treatment of depression and/or anxiety. Such combined preparations may be, for example, in the form of a twin pack. It will also be appreciated that a compound of the present invention and one or more of the other agents may be administered as separate pharmaceutical compositions, either simultaneously or sequentially.

The invention therefore relates to a pharmaceutical composition according to the invention, characterized in that is comprises further one or more other compounds selected from the group of antidepressants, anxiolytics and antipsychotics.

Suitable classes of antidepressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), noradrenergic and specific serotonergic antidepressants (NaSSAs), corticotropin releasing factor (CRF) antagonists, α-adrenoreceptor antagonists and atypical antidepressants.

Suitable examples of norepinephrine reuptake inhibitors include amitriptyline, clomipramine, doxepin, imipramine, trimipramine, amoxapine, desipramine, maprotiline, nortriptyline, protriptyline, reboxetine and pharmaceutically acceptable salts thereof.

Suitable examples of selective serotonin reuptake inhibitors include fluoxetine, fluvoxamine, paroxetine, sertraline and pharmaceutically acceptable salts thereof. Suitable examples of monoamine oxidase inhibitors include isocarboxazid, phenelzine, tranylcypromine, selegiline and pharmaceutically acceptable salts thereof.

Suitable examples of reversible inhibitors of monoamine oxidase include moclobemide and pharmaceutically acceptable salts thereof.

Suitable examples of serotonin and noradrenaline reuptake inhibitors include venlafaxine and pharmaceutically acceptable salts thereof.

Suitable atypical antidepressants include bupropion, lithium, nefazodone, trazodone, viloxazine, sibutramine and pharmaceutically acceptable salts thereof.

Other suitable antidepressants include adinazolam, alaproclate, amineptine, amitriptyline/chlordiazepoxide combination, atipamezole, azamianserin, bazinaprine, befuraline, bifemelane, binodaline, bipenamol, brofaromine, bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, monirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, tofenacin, tofisopam, toloxatone, tomoxetine, veralipride, viqualine, zimelidine and zometapine and pharmaceutically acceptable salts thereof, and St. John's wort herb, or Hypericum perforatum, or extracts thereof.

Suitable classes of anti-anxiety agents include benzodiazepines and 5-HT$_{1A}$ receptor agonists or antagonists, especially 5-HT$_{1A}$ partial agonists, corticotropin releasing factor (CRF) antagonists, compounds having muscarinic cholinergic activity and compounds acting on ion channels. In addition to benzodiazepines, other suitable classes of anti-anxiety agents are nonbenzodiazepine sedative-hypnotic drugxs such as zolpidem; mood-stabilizing drugs such as clobazam, gabapentin, lamotrigine, loreclezole, oxcarbamazepine, stiripentol and vigabatrin; and barbiturates.

Suitable antipsychotic agents are selected from the group of acetophenazine, in particular the maleate salt; alentemol, in particular the hydrobromide salt; alpertine; azaperone; batelapine, in particular the maleate salt; benperidol; benzindopyrine, in particular the hydrochloride salt; brofoxine; bromperidol; butaclamol, in particular the hydrochloride salt; butaperazine; carphenazine, in particular the maleate salt; carvotroline, in particular the hydrochloride salt; chlorpromazine; chlorprothixene; cinperene; cintriamide; clomacran, in particular the phosphate salt; clopenthixol; clopimozide; clopipazan, in particular the mesylate salt; cloroperone, in particular the hydrochloride salt; clothiapine; clothixamide, in particular the maleate salt; clozapine; cyclophenazine, in particular the hydrochloride salt; droperidol; etazolate, in particular the hydrochloride salt; fenimide; flucindole; flumezapine; fluphenazine, in particular the decanoate, enanthate and/or hydrochloride salts; fluspiperone; fluspirilene; flutroline; gevotroline, in particular the hydrochloride salt; halopemide; haloperidol; iloperidone; imidoline, in particular the hydrochloride salt; lenperone; loxapine; mazapertine, in particular the succinate salt; mesoridazine; metiapine; milenperone; milipertine; molindone, in particular the hydrochloride salt; naranol, in particular the hydrochloride salt; neflumozide, in particular the hydrochloride salt; ocaperidone; olanzapine; oxiperomide; penfluridol; pentiapine, in particular the maleate salt; perphenazine; pimozide; pinoxepin, in particular the hydrochloride salt; pipamperone; pipeacetazine; pipotiazine, in particular the palmitate salt; piquindone, in particular the hydrochloride salt; prochlorperazine, in particular the edisylate salt; prochlorperazine, in particular the maleate salt; promazine, in particular the hydrochloride salt; quetiapine; remoxipride; risperidone; rimcazol, in particular the hydrochloride salt; seperidol, in particular the hydrochloride salt; sertindole; setoperone; spiperone; sulpiride; thioridazine; thiothixene; thorazine; tioperidone, in particular the hydrochloride salt; tiospirone, in particular the hydrochloride salt; trifluoperazine, in particular the hydrochloride salt; trifluperidol; triflupromazine; ziprasidone, in particular the hydrochloride salt; and mixtures thereof.

A compound according to the invention, in particular according to Formula (I) may also be used in conjunction with other lipid-lowering agent, thus leading to a so-called combination lipid-lowering therapy for the treatment of obesity. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors, CB-1 antagonists, cholesterol absorption inhibitors such as ezetimibe, and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the bio-transformation of hydroxymethylglutaryl-coenzyme A to mevalonic acid as catalyzed by the enzyme HMG-CoA reductase. Such "HMG-CoA reductase inhibitors" are, for example, lovastatin, simvastatin, fluvastatin, pravastatin, rivastatin, and atorvastatin.

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase Any HMG-CoA reductase gene expression inhibitor may be used as the second compound in the combination therapy aspect of this invention. These agents may be HMG-CoA reductase trancription inhibitors that block the transcription of DNA or translation inhibitors that prevent translation of mRNA coding for HMG-CoA reductase into protein. Such inhibitors may either affect trancription or translation directly or may be biotransformed into compounds having the above-mentioned attributes by one or more enzymes in the cholesterol biosynthetic cascade or may lead to accumulation of a metabolite having the above-mentioned activities.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, an N-oxide form thereof or a quaternary ammonium salt thereof.

A compound according to the invention, in particular a compound according to Formula (I), the pharmaceutically acceptable acid or base addition salt thereof, an N-oxide form thereof or a quaternary ammonium salt thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. Since the compounds according to the invention are potent orally administrable dopamine antagonists, pharmaceutical compositions comprising said compounds for administration orally are especially advantageous.

As already mentioned, the invention also relates to a pharmaceutical composition comprising a compound according to the invention and one or more other compounds selected from the group of antidepressants, anxiolytics, antipsychotics and lipid-lowering agents as well as to the use of such a composition for the manufacture of a medicament.

The following examples are intended to illustrate but not to limit the scope of the present invention.

Experimental Part

Throughout the whole of this application, "THF" means tetrahydrofuran; "DMF" means N,N-dimethylformamide; "EtOAc" means ethyl acetate; "DCM" means dichloromethane; "DME" means 1,2-dimethoxyethane; "DCE" means 1,2-dichloroethane; "DIPE" means diisopropylether; "DMSO" means dimethylsulfoxide; "DIPEA" means diisopropylethylamine; "DIAD" means diisopropyl diazodicarboxylate; "TEMPO" means 2,2,6,6-tetramethylpiperidin-1-oxyl Free Radical; "BINAP" means 2,2'-bis(diphenylphosphino)-1,1'-binaphthyl; "TFA" means trifluoroacetic acid; "Xantphos" means 4,5-bis(diphenylphosphino)-9,9-dimethylxanthene; "BOC" means tert-butyloxycarbonyl; "NMO" means N-methylmorpholine-N-oxide.

Microwave assisted reactions were performed in a single-mode reactor: Emrys™ Optimizer microwave reactor (Personal Chemistry A.B., urrently Biotage) or Initiator™ Sixty (Biotage). Description of both instruments can be found in www.biotage.com. And in a multimode reactor:

MicroSYNTH Labstation (Milestone, Inc.). Description of the instrument can be found in www.milestonesci.com.

A. Preparation of the Intermediate Compounds

A1. Preparation of Intermediate Compound I-1

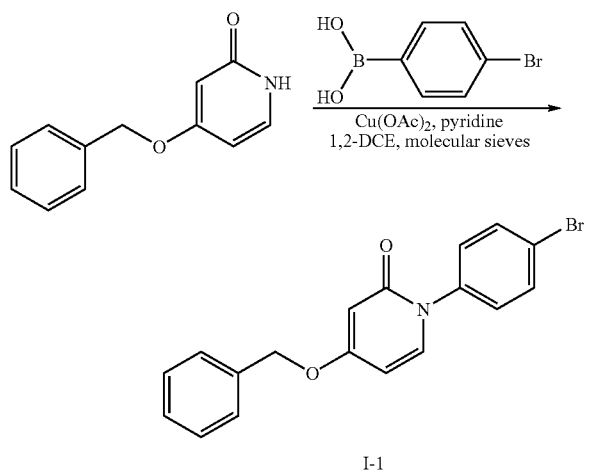

I-1

To a solution of 4-benzyloxy-2(1H)-pyridone (1 g, 5.0 mmol) in DCE (20 ml), was added 4-bromophenylboronic acid (2 g, 12.0 mmol), Cu(OAc)$_2$ (1.82 g, 10.0 mmol), pyridine (1.51 ml, 20.0 mmol) and molecular sieves (4 Å) (2 g). The reaction mixture was heated under microwave irradiation at 180° C. for 15 min. The solid was filtered off. The filtrate was treated with an aqueous solution of NH$_4$OH. The organic layer was separated, dried (Na$_2$SO$_4$) and the solvent evaporated. The resulting residue was purified by column chromatography in DCM 100 to DCM/EtOAc 4:1 to yield intermediate compound I-1 (230 mg, 13%).

A2. Preparation of Intermediate Compound I-2

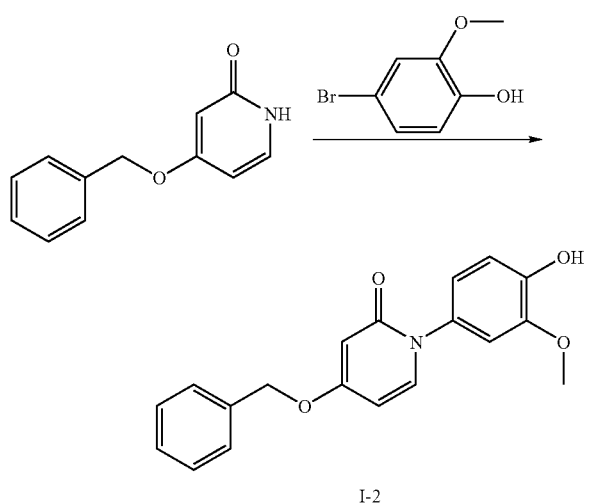

I-2

A mixture of 4-benzyloxy-2(1H)-pyridone (0.5 g, 0.0025 mol), 4-bromo-2-methoxyphenol (0.67 g, 0.0033 mol), CuI (0.48 g, 0.0025 mol)), N,N'-dimethylethylenediamine (0.53 ml, 0.0050 mol) and K$_3$PO$_4$ (1.06 g, 0.0050 mol) in dioxane/DMF (4/1; 10 ml) was heated for 15 minutes at 180° C. in a microwave oven. Subsequently heating was repeated again for 15 minutes in a microwave. The solid was filtered off and the filter was washed with DCM. A NH$_4$OH solution (32%) was added to the filtrate. The organic layer was separated, dried (Na$_2$SO$_4$), filtered and the solvent was evaporated. The residue was purified by flash column chromatography. The desired fractions were collected and the solvent was evaporated. The residue was precipitated with DIPE, yielding intermediate compound I-2 (31%).

A3. Preparation of Intermediate Compound I-3

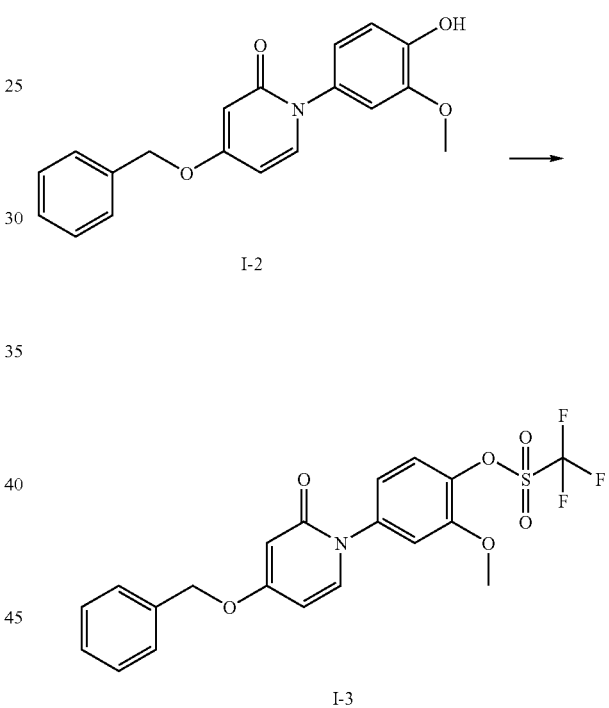

I-3

A mixture of intermediate compound 1-2 (0.76 g, 0.0033 mol), 1,1,1-trifluoro-N-phenyl-N-[(trifluoromethyl)sulfonyl]-methanesulfonamide (1.18 g, 0.0033 mol) and K$_2$CO$_3$ (1.38 g, 0.01 mol) in THF (20 ml) was heated in a microwave at 120° C. for 15 minutes. The solid was filtered off and washed with DCM. The filtrate was evaporated. The residue was purified by flash column chromatography over silica gel (eluent: DCM/EtOAc 100/0, 9/1 and 4/1). The desired fractions were collected and the solvent was evaporated. Yield: 0.9 g of intermediate compound I-3 (60%).

Intermediate compound I-3 can also be obtained by adding trifluoromethanesulfonic anhydride (1.1 eq) at 0° C. to a mixture of intermediate compound 1-2, Et$_3$N and DCM as the solvent. In this case the mixture is stirred for 2 hours at room temperature to complete reaction.

A4. Preparation of Intermediate Compound I-4

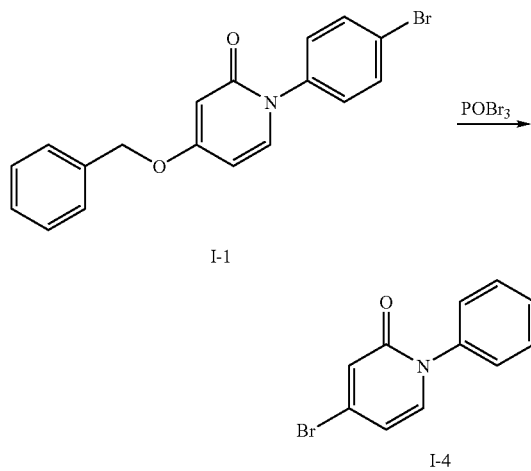

A mixture of I-1 (534 mg, 0.0015 mol) and POBr$_3$ (1.72 g, 0.006 mol) in 1,2-DCE (7.5 ml) was stirred in a microwave at 150° C. for 20 minutes. Then, Na$_2$CO$_3$ (aqueous saturated solution), DCM and MeOH were added. The reaction mixture was stirred until clear mixtures of the solution was obtained. Then, the organic layer was separated, dried (Na$_2$SO$_4$) and the solvent was evaporated. The residue was purified by flash column chromatography over silica gel (eluent: DCM and DCM/EtOAc; 9/1). Afterwards, the residue was treated with DIPE, yielding 0.375 g of intermediate compound I-4 (76%) as a solid.

A5. Preparation of Intermediate Compound I-5

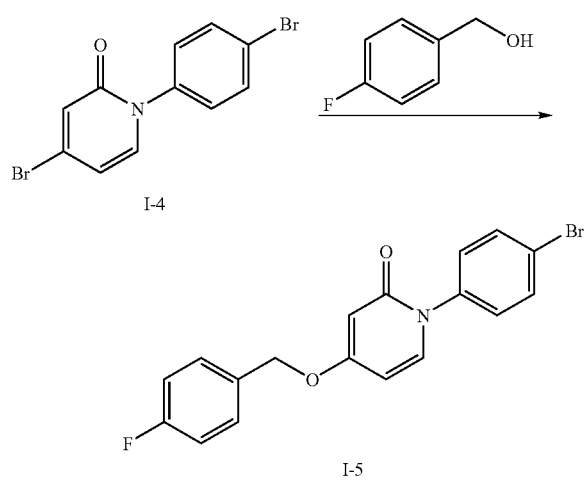

To NaH 60% (55 mg, 0.00136 mol) in DME (1.5 ml), 4-fluorobenzyl alcohol (0.149 ml, 0.00136 mol) was added dropwise at 0° C. The reaction mixture was stirred at room temperature for 15 minutes. Then, I-4 (225 mg, 0.00068 mol) in DME (1.5 ml) was added. The reaction mixture was stirred in a microwave at 120° C. for 10 minutes. Afterwards, NH$_4$Cl (10%) and DCM were added. The organic layer was separated, dried (Na$_2$SO$_4$) and the solvent was evaporated. The residue was purified by flash column chromatography over silica gel (eluent: DCM and DCM/EtOAc 9/1 and 4/1), yielding 0.193 g of intermediate compound I-5 (76%).

A6. Preparation of Intermediate Compound I-6

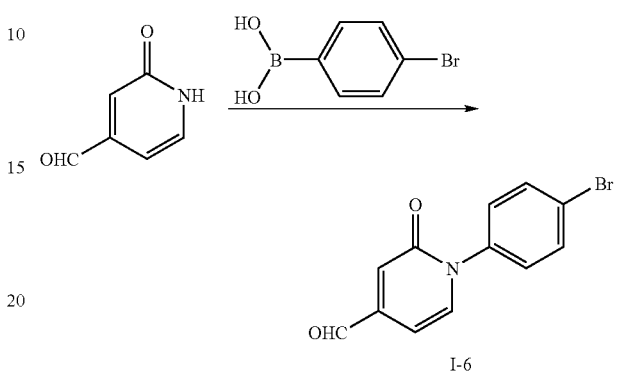

A mixture of 2-hydroxy-4-pyridinecarboxaldehyde (123 mg, 0.001 mol), 4-bromo-phenylboronic acid (400 mg, 0.002 mol), Cu(OAc)$_2$ (18 mg, 0.0001 mol), pyridine (162 ml, 0.002 mol), TEMPO (172 mg, 0.0011 mol) and molecular sieves in DCM (2 ml) was stirred at room temperature for 24 hours. Then, the solids were filtered through a celite pad and the filtrate was treated with Na$_2$CO$_3$ (aqueous saturated solution). The organic layer was separated, dried over Na$_2$SO$_4$ and the solvent evaporated. The residue was purified by column chromatography (eluents: DCM and DCM/EtOAc; 9/1), yielding 0.180 g of intermediate compound I-6 (65%).

A7. Preparation of Intermediate Compound I-7

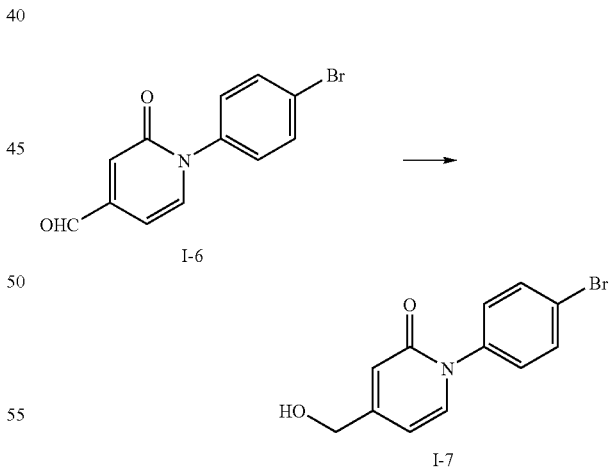

To a mixture of intermediate I-6 (180 mg, 0.00065 mol) in methanol (5 ml), sodium borohydride (30 mg, 0.00078 mol) was added at 0° C. The reaction was stirred at room temperature for 30 minutes. Then NH$_4$Cl (aqueous saturated solution) was added. The mixture was extracted with DCM. The organic layer was separated, dried over Na$_2$SO$_4$ and the solvent evaporated. The residue was precipitated with DIPE, yielding 0.170 g of intermediate compound I-7 (93%).

A8. Preparation of Intermediate Compound I-8

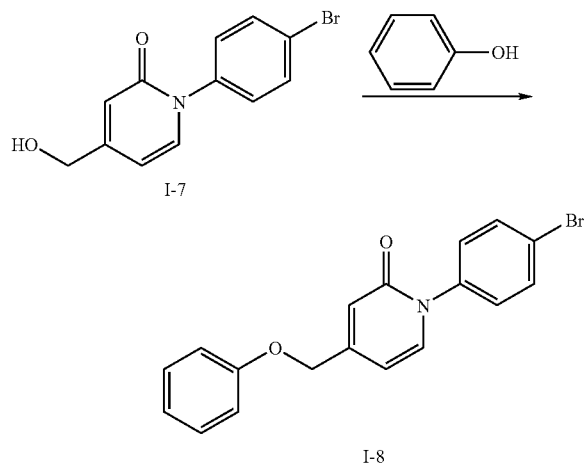

A mixture of compound I-7 (170 mg, 0.00061 mol), phenol (87 mg, 0.00092 mol), DIAD (181 ml, 0.00092 mol), and triphenylphosphine (241 mg, 0.00092 mol) in THF (2 ml) was stirred in a microwave at 100° C. for 10 minutes. The solvent was evaporated and the residue was purified by column chromatography (eluent: DCM and DCM/EtOAc 9/1). Then the residue was treated with DIPE, yielding 0.151 g of intermediate compound I-8 (70%).

A9. Preparation of Intermediate Compound I-9

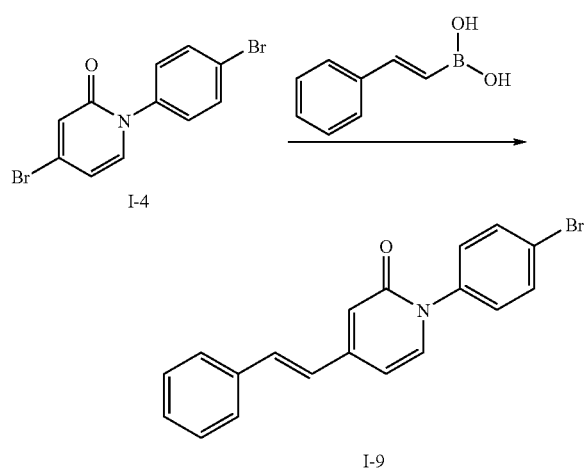

A mixture of compound I-4 (150 mg, 0.00045 mol), trans-2-phenylvinylboronic acid (66 mg, 0.00045 mol) and Pd(PPh$_3$)$_4$ (27 mg, 0.000023 mol) in deoxigenated dioxane (1 ml) and Na$_2$CO$_3$ aq. saturated (1 ml) was stirred in a microwave at 150° C. for 10 minutes. Then, DCM and H$_2$O were added. The organic layer was separated, dried over Na$_2$SO$_4$ and the solvent evaporated. The residue was purified by flash column chromatography over silica gel (eluent: DCM and DCM/EtOAc; 9/1 and 4/1), yielding 0.040 g of intermediate compound 1-9 (25%).

A10. Preparation of Intermediate Compound I-10

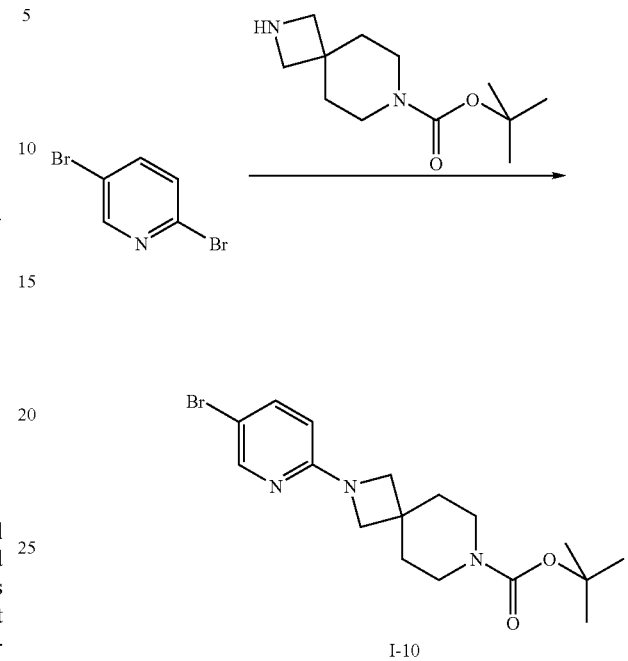

A mixture of 2,5-dibromopyridine (474 mg, 0.0002 mol), 2,7-diazaspiro[3.5]nonane-7-carboxylic acid, 1,1-dimethyl-ethyl ester (CAS: 896464-16-7, 500 mg, 0.00019 mol), DIPEA (2 ml) in acetonitrile (1 ml) was heated at 175° C. under microwave irradiation for 10 minutes. Then DCM and Na$_2$CO$_3$ (aqueous saturated solution) were added. The organic layer was separated, dried over Na$_2$SO$_4$, filtered and the filtrate was concentrated. The residue was purified by flash chromatography (eluent: DCM and DCM/EtOAc 4:1) to obtain 375 mg of intermediate compound I-10 (52%).

A11. Preparation of Intermediate Compound I-11

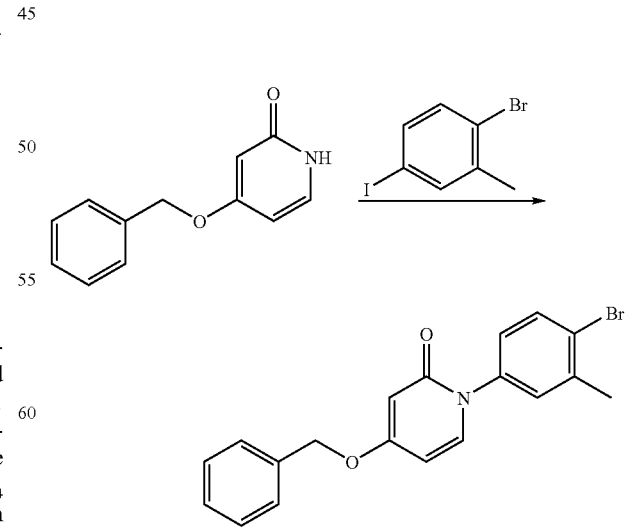

A mixture of 4-benzyloxy-2(1H)-pyridone (50 mg, 0.0025 mol), 2-bromo-5-iodotoluene (1.13 g, 0.0038 mol), CuI (0.238 g, 0.0015 mol), N,N-dimethylethylenediamine (0.266 ml, 0.0025 mol), and $K_3PO_4$ (1.06 g, 0.005 mol) in dioxane/DMF 9:1 (75 ml) was stirred at 180° C. in a microwave for 15 minutes Then, DCM was added. The solid was filtered off through dicalite and the filtrate was washed with $NH_4OH$ 32%. The organic layer was separated, dried over $Na_2SO_4$ and the solvent was evaporated. The residue was purified by column chromatography (eluent: DCM). The desired product was collected and evaporated. The resulting product was precipitated with DIPE yielding 0.737 g of intermediate compound I-11 (80%).

B. Preparation of the Final Compounds

B1. Preparation of Final Compound I-5

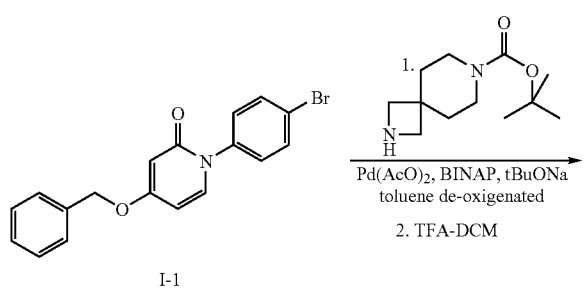

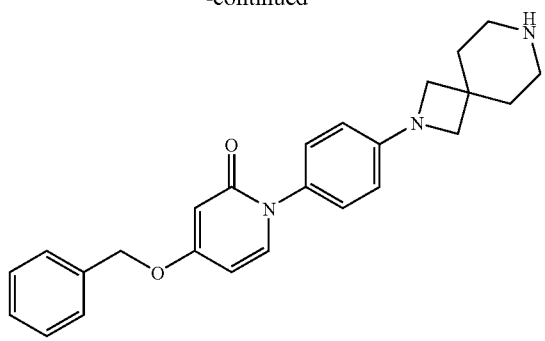

1-5

To a mixture of intermediate compound I-1 (0.000561 mol) in toluene (3 ml) under $N_2$ atmosphere was added 2,7-diazaspiro[3.5]nonane-7-carboxylic acid, 1,1-dimethylethyl ester (CAS: 896464-16-7, 0.00078 mol), $Pd(OAc)_2$ (0.0000267 mol), BINAP (0.000042 mol) and finally $^tBuONa$ (0.00168 mol). The mixture was refluxed in a sealed tube overnight. Then, $H_2O$ was added to the mixture and extracted with DCM. The organic layer was filtered, dried over $Na_2SO_4$ and concentrated. The residue was purified by flash column chromatography over silica gel (10 g cartridge; eluent: DCM and DCM/($CH_3OH/NH_3$); 10% to 30%) to obtain 0.189 g of a BOC-protected compound (67%). This compound (0.00717 mol) was dissolved in TFA (14 ml) and DCM (28.8 ml). The reaction mixture was stirred at room temperature for 2 hours. The solvent was concentrated and the residue was neutralized with NaOH 50% under ice cool bath. The organic phase was extracted with DCM, dried over $Na_2SO_4$ and evaporated. The residue was purified by short column chromatography over silica gel (eluent: $DCM/CH_3OH$; 9.5/0.5 and $DCM/(CH_3OH(NH_3)$; from 9.5/0.5 to 9/1), yielding 1.08 g of compound I-5 (49%).

B2. Preparation of Final Compound I-11

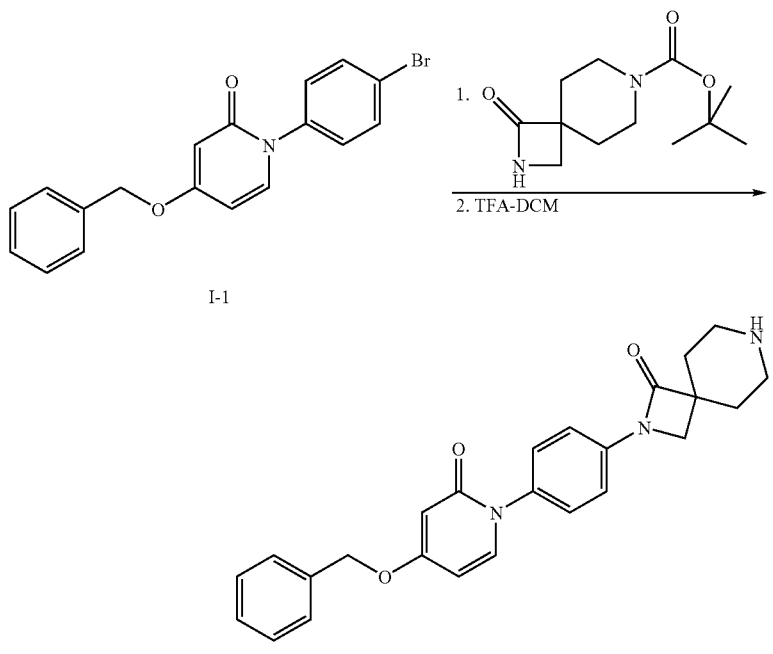

A mixture of intermediate compound I-1 (0.00084 mol), 1-oxo-2,7-diaza-spiro[3.5]nonane-7-carboxylic acid tert-butyl ester (024 g, 0.0010 mol), CuI (0.16 g, 0.00084 mol), N,N-dimethylethylenediamine (0.0016 mol), and K₃PO₄ (0.35 g, 0.0016 mol) in dioxane/DMF 9:1 (75 ml) was stirred at 175° C. in a microwave for 20 minutes. Then, DCM was added. The solid was filtered off through dicalite and the filtrate was washed with NH₄Cl (aqueous saturated solution) The organic layer was separated, dried over Na₂SO₄ and the solvent was evaporated to obtain 0.433 g of the BOC-protected compound. This crude product (0.000969 mol) was dissolved in TFA (2 ml) and DCM (4 ml). The reaction mixture was stirred at room temperature for 2 hours. After this time the reaction was neutralized with Na₂CO₃ (saturated aqueous solution) under ice-cool bath conditions. The organic phase was extracted with DCM, dried over Na₂SO₄ and evaporated. The residue was purified by short column chromatography over silica gel (5 g), and washed with ethyl ether, yielding 0.270 g of compound. 1-11 (67%).

B3. Preparation of Final Compound 2-1

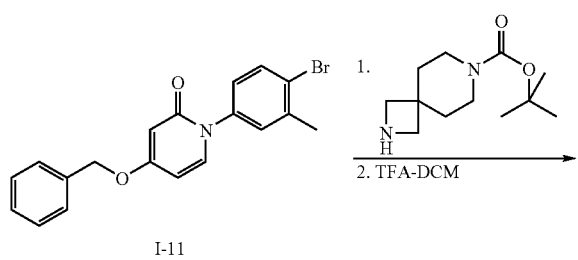

I-11

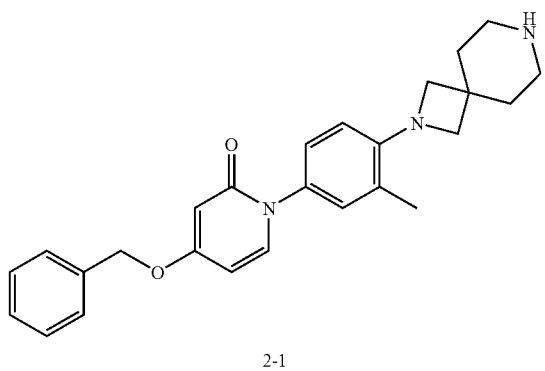

2-1

A mixture of intermediate compound I-11 (185 mg, 0.0005 mol), 2,7-diazaspiro[3.5]-nonane-7-carboxylic acid, 1,1-dimethylethyl ester (CAS: 896464-16-7, 171 mg, 0.00065 mol), Pd(OAc)₂ (11 mg, 0.00005 mol), BINAP (23 mg, 0.0375 mmol), and ᵗBuONa (144 mg, 0.0015 mol) in toluene (2.5 ml) was stirred under N₂ atmosphere and heated at 100° C. for 24 hours. Excess of Pd(OAc)₂ and BINAP were added while heating the reaction for 24 hours more. Then DCM was added. The solids were filtered off through celite and the filtrate was evaporated. The residue was purified by flash column chromatography over silica gel (eluent: DCM and DCM/EtOAc; 9/1 and DCM/Acetone 9/1 and 4/1), yielding 0.175 g of the BOC-protected compound. This compound was dissolved in TFA (1 ml) and DCM (2 ml) and the reaction mixture was stirred at room temperature for 2 hours. Then, Na₂CO₃ (saturated aqueous solution) was added. The organic layer was separated, dried over Na₂SO₄ and the solvent was evaporated. The residue was purified by flash column chromatography over silica gel (eluent: DCM/MeOH 95/5 and DCM/(CH₃OH/NH₃); 95/5). The residue was treated with ethyl ether, yielding 0.089 g of compound 2-1 (62%).

B4. Preparation of Final Compound 2-2

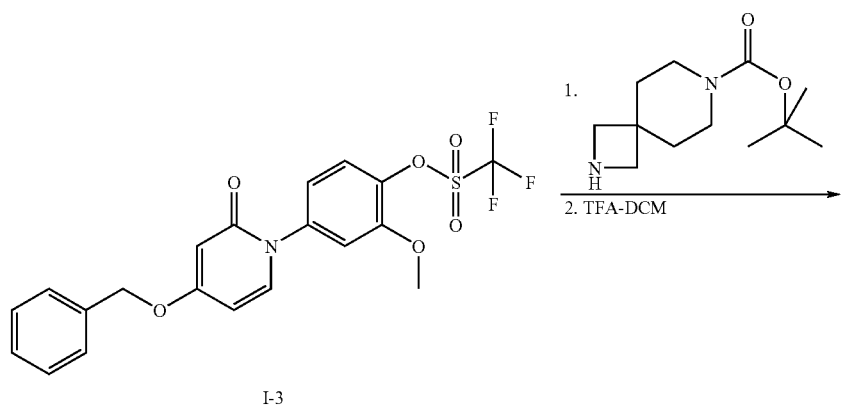

I-3

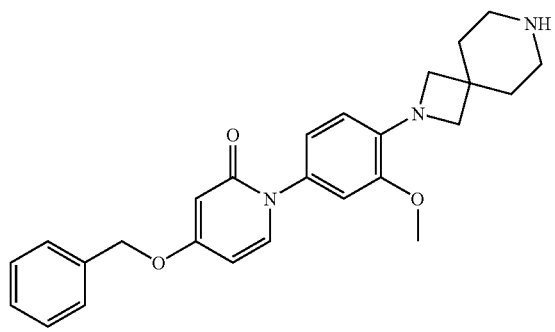

2-2

A mixture of intermediate compound I-3 (228 mg, 0.0005 mol), 2,7-diazaspiro[3.5]nonane7-carboxylic acid, 1,1-dimethylethyl ester (CAS: 896464-16-7, 171 mg, 0.00065 mol), Pd(OAc)$_2$ (11 mg, 0.00005 mol), Xantphos (58 mg, 0.0001 mol), and Cs$_2$CO$_3$ (407 mg, 0.00125 mol) in trifluorotoluene (3.0 ml) was stirred under N$_2$ atmosphere and heated at 100° C. for 24 hours. Then DCM was added. The solids were filtered off through celite and the filtrate was evaporated. The residue was purified by flash column chromatography over silica gel (eluent: DCM and DCM/EtOAc; 9/1 and DCM/Acetone 9/1 and 4/1), yielding 0.130 g of the BOC-protected compound. This compound was solved in TFA (1 ml) and DCM (2 ml) and the reaction mixture was stirred at room temperature for 2 hours. Then, Na$_2$CO$_3$ (saturated aqueous solution) was added. The organic layer was separated, dried over Na$_2$SO$_4$ and the solvent was evaporated. The residue was purified by flash column chromatography over silica gel (eluent: DCM(MeOH) 95/5 and DCM/(CH$_3$OH/NH$_3$); 95/5). The residue was treated with ethyl ether, yielding 0.0366 g of compound 2-2 (35%).

B5. Preparation of Final Compound 3-2

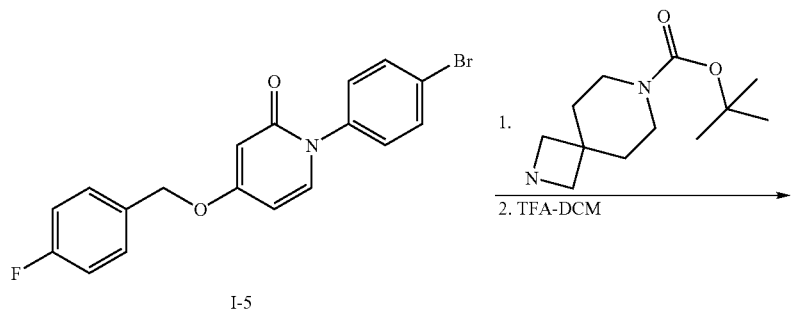

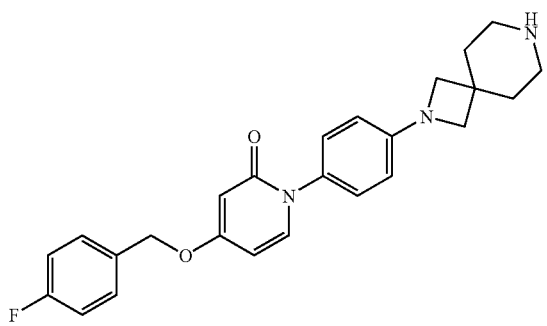

3-2

A mixture of intermediate compound I-5 (0.190 g, 0.00051 mol), 2,7-diazaspiro[3.5]nonane-7-carboxylic acid, 1,1-dimethylethyl ester (CAS: 896464-16-7, 0.177 g, 0.00066 mol), Pd(OAc)$_2$ (58 mg, 0.000026 mol), BINAP (24 mg, 0.000038 mol), and $^t$BuONa (147 mg, 0.00153 mol) in deoxigenated toluene (4 ml) was heated overnight at 100° C. Then, DCM was added. The solid was filtered off and the filtrate was evaporated. The residue was purified by flash column chromatography over silica gel (eluent: DCM and DCM/Acetone; 9/1 and 4/1), yielding 0.202 g of a the BOC-protected compound. This compound (0.202 g, 0.00039 mol) was dissolved in TFA (2 ml) and DCM (4 ml) and stirred at room temperature for 2 hours. Then, Na$_2$CO$_3$ (saturated aqueous solution) was added. The organic layer was separated, dried over Na$_2$SO$_4$ and the solvent was evaporated. The residue was purified by flash column chromatography over silica gel (eluent: DCM(MeOH) 95/5 and DCM/(CH$_3$OH/NH$_3$); 9/1). Afterwards the residue was treated with DIPE, yielding 0.098 g of compound 3-2 (60%).

B6. Preparation of Final Compound 3-1

A mixture of intermediate compound I-9 (0.040 g, 0.00011 mol), 2,7-diazaspiro[3.5]-nonane7-carboxylic acid, 1,1-dimethylethyl ester (CAS: 896464-16-7, 0.037 g, 0.00014 mol), Pd(OAc)$_2$ (12 mg, 0.0000055 mol), BINAP (5 mg, 0.0000083 mol) and $^t$BuONa (0.00033 mol) in toluene (1 ml) was stirred under N$_2$ atmosphere and heated overnight at 100° C. Then, DCM was added. The solid was filtered off through celite and the solvent was evaporated. The residue was purified by flash column chromatography over silica gel (eluent: DCM and DCM/Acetone 9/1), yielding 0.050 g of the BOC-protected amine (91%). This product was dissolved in a mixture of TFA (0.5 ml) and DCM (1 ml), stirring the reaction mixture at room temperature for 2 hours. Then, Na$_2$CO$_3$ (aqueous saturated solution) was added. The organic layer was separated, dried over Na$_2$SO$_4$ and the solvent evaporated. The residue was purified by flash column chromatography over silica gel (eluent: DCM(CH$_3$OH) 95/5 and DCM/(CH$_3$OH/NH$_3$); 1/1). The residue was treated with DIPE, yielding 0.017 g of compound 3-1 (43%).

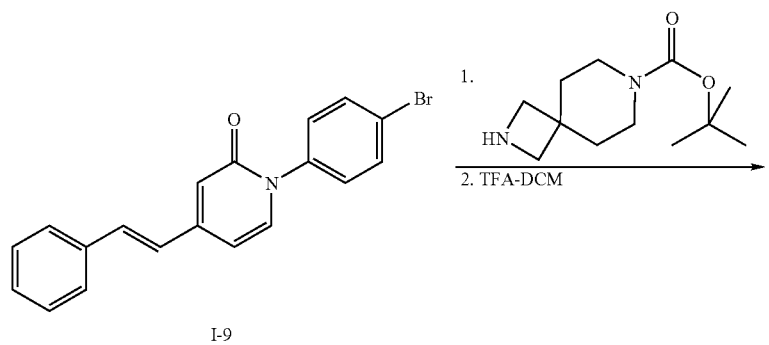

I-9

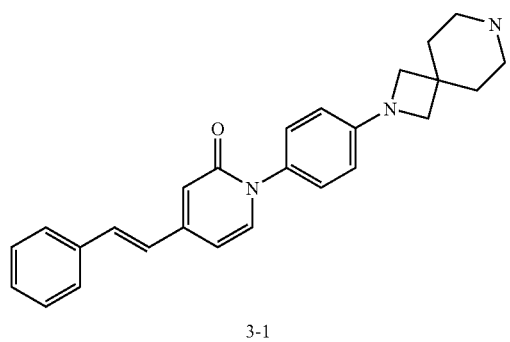

3-1

B7. Preparation of Final Compound 3-3

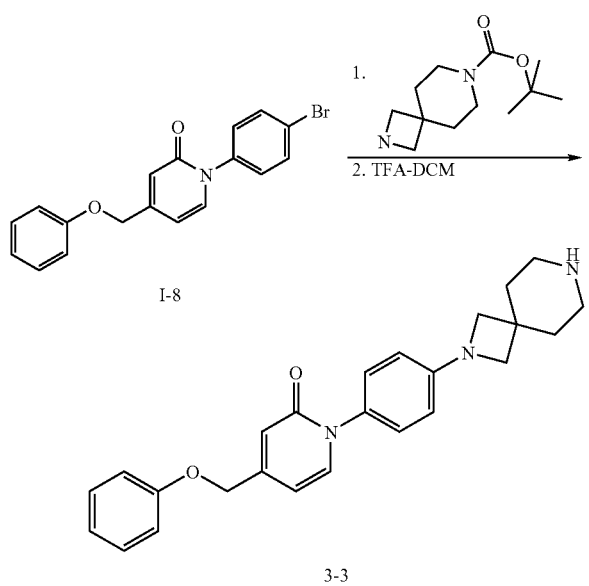

A mixture of intermediate compound I-8 (304 mg, 0.00085 mol), 2,7-diazaspiro[3.5]nonane7-carboxylic acid, 1,1-dimethylethyl ester (CAS: 896464-16-7, 289 mg, 0.0011 mol), Pd(OAc)$_2$ (10 mg, 0.000043 mol), BINAP (40 mg, 0.000064 mol) and $^t$BuONa (245 mg, 0.00255 mol) in toluene (5 ml) was heated at 100° C. for 24 hours. Then DCM was added. The solid was filtered through celite pad. The filtrate was evaporated, dried over MgSO$_4$ and the residue was purified by column chromatography (eluent: DCM and DCM/Acetone; 9/1), yielding 0.430 g of the BOC-protected amine. This compound was dissolved in TFA (2 ml) and DCM (4 ml) and the mixture was shaken at room temperature for 2 hours. Then, Na$_2$CO$_3$ (saturated aqueous solution) was added. The organic layer was separated, dried over Na$_2$SO$_4$, and the solvent evaporated. The residue was treated with ethyl ether, yielding 0.278 g of compound 3-3 (81%).

B8. Preparation of Final Compound 4-1

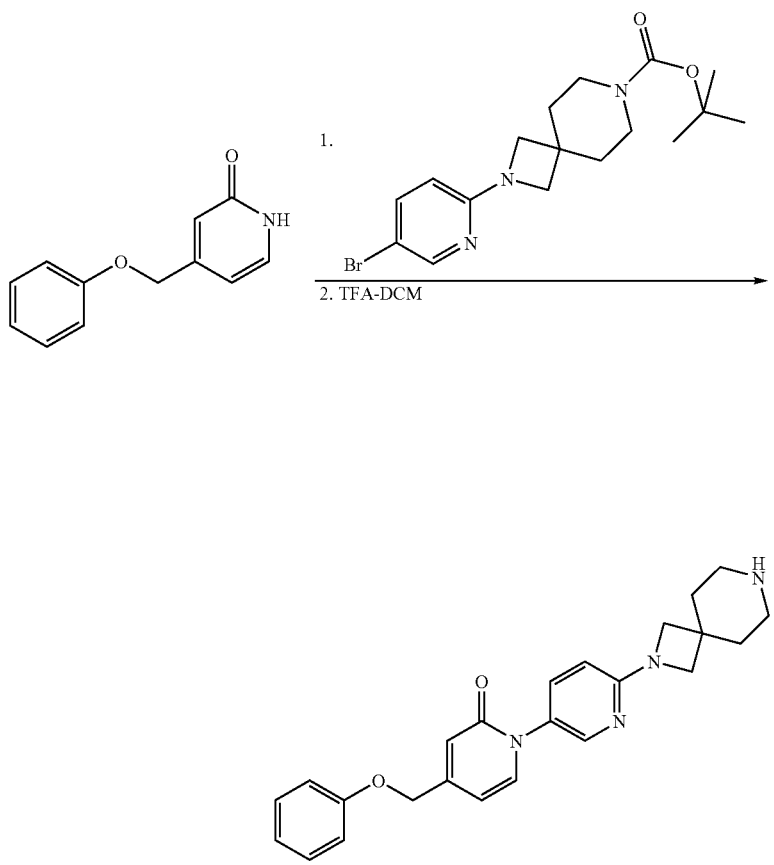

A mixture of 4-benzyloxy-2(1H)-pyridone (187 mg, 0.93 mmol), intermediate compound I-10 (375 mg, 0.93 mmol), copper iodide (177 mg, 0.93 mmol), N,N-dimethylethylendiamine (0.198 ml, 1.86 mmol), potassium phosphate (395 mg, 1.86 mmol) in dioxane:DMF 4:1 (4 ml) was heated at 180° C. for 15 min. under microwave irradiation. Then DCM was added. The solid was filtered off through a celite pad. The filtrate was treated with a solution of $NH_4OH$ (30%). The organic layer was separated, dried ($Na_2SO_4$) and the solvent was evaporated to afford 600 mg of the BOC-protected compound. This compound was dissolved in TFA (3 ml) and DCM (6 ml) and the mixture was shaken at room temperature for 1 hour. Then, $Na_2CO_3$ (saturated aqueous solution) was added. The organic layer was separated, dried over $Na_2SO_4$, and the solvent evaporated. The residue was purified by column chromatography (eluents: $DCM/CH_3OH$ 98/5 and $DCM/CH_3OH(NH_3)$ 9/1). The desired fractions were collected and the solvent evaporated. The residue was treated with ethyl ether, yielding 0.238 g of compound 4-1 (64%).

B9. Preparation of Final Compound 1-9

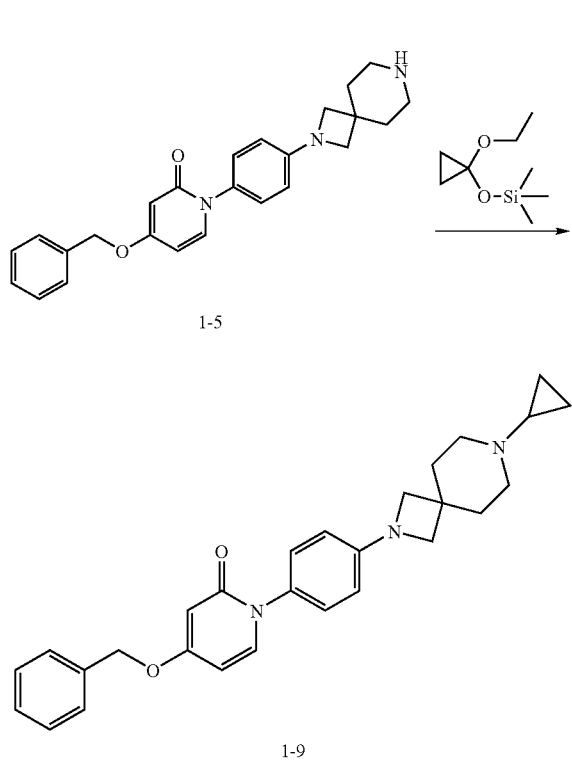

1-5

1-9

A mixture of compound 1-5 (0.5 g, 1.25 mmol) and 1-ethoxy-1-[(trimethylsilyl)oxy]-cyclopropane (0.260 ml, 0.0013 mol) in MeOH (methanol; 6 ml) and acetic acid (0.2 ml) was stirred at room temperature for 30 minutes. Then sodium cyanoborohydride (0.113 g, 0.0018 mol) was added. The reaction mixture was heated at 80° C. for 24 hours. Then $NaHCO_3$ (aqueous saturated solution) and $NH_4OH$ (30%) were added. The mixture was extracted with DCM. The separated organic layer was dried ($Na_2SO_4$) and the solvent was evaporated. The residue was purified by flash column chromatography over silica gel (eluent: DCM/MeOH 95/5 and DCM/(MeOH/$NH_3$) 95/5. The desired fractions were collected and the solvent was evaporated. The residue was treated with ethyl ether, yielding 0.470 g of compound 1-9 (86%).

B10. Preparation of Final Compound 2-4

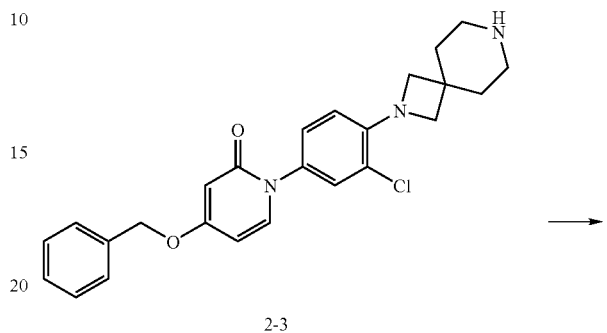

2-3

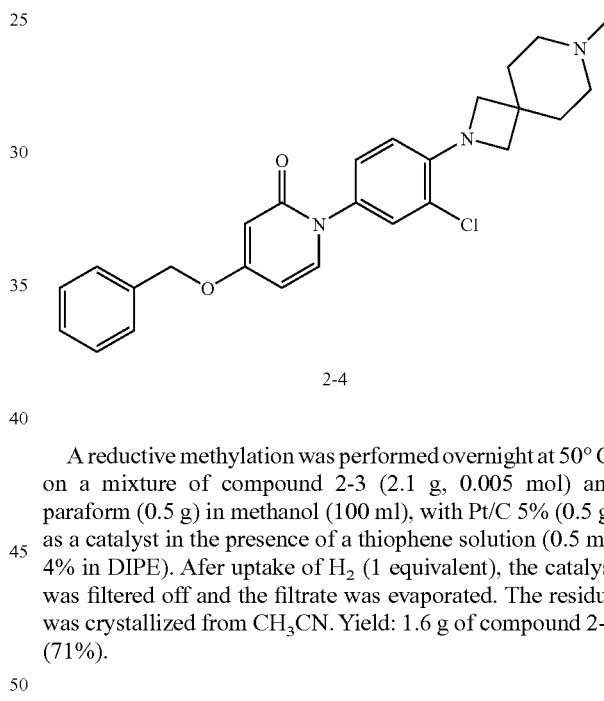

2-4

A reductive methylation was performed overnight at 50° C. on a mixture of compound 2-3 (2.1 g, 0.005 mol) and paraform (0.5 g) in methanol (100 ml), with Pt/C 5% (0.5 g) as a catalyst in the presence of a thiophene solution (0.5 ml; 4% in DIPE). Afer uptake of $H_2$ (1 equivalent), the catalyst was filtered off and the filtrate was evaporated. The residue was crystallized from $CH_3CN$. Yield: 1.6 g of compound 2-4 (71%).

B11. Preparation of Final Compound 1-15

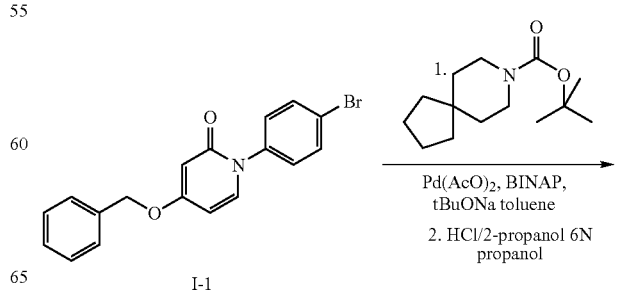

I-1

Pd(AcO)$_2$, BINAP, tBuONa toluene

2. HCl/2-propanol 6N propanol

-continued

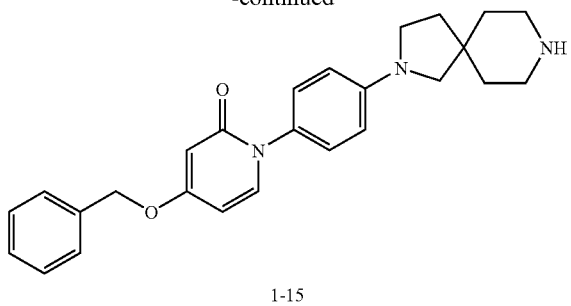

1-15

A mixture of intermediate compound I-1 (7.80 g, 0.022 mol), 2,8-diazaspiro[4.5]decane-8-carboxylic acid, 1,1-dimethylethyl ester (6 g, 0.025 mol), Pd(OAc)$_2$ (0.25 g, 0.0011 mol), BINAP (1.12 g, 0.0018 mol) and $^t$BuONa (2.4 g, 0.025 mol) was stirred overnight under N$_2$ atmosphere in an oil bath at 100° C. Subsequently the reaction mixture was cooled to room temperature and was filtered over Dicalite. The filter was washed with toluene (200 ml). The filtrate was evaporated and yielded 6 g of crude residue. The filter was also washed with hot DCM (300 ml). The solvent was evaporated, yielding 12 g of a white solid. The combined residues were crystallized from CH$_3$CN. 8.3 g of a BOC-protected compound was obtained (73%). This BOC-protected compound (8.3 g, 0.016 mol) was suspended in 2-propanol (200 ml). Then HCl/2-propanol (50 ml; 6 N) was added and a solution was obtained. This solution was heated and a precipitate occurred. The mixture was refluxed for 3 hours after which it was cooled on an ice-bath. The product was filtered off. Yield: 8.0 g of compound 1-15 (99%;. 2HCl. 0.8 H$_2$O).

B12. Preparation of Final Compound 1-14

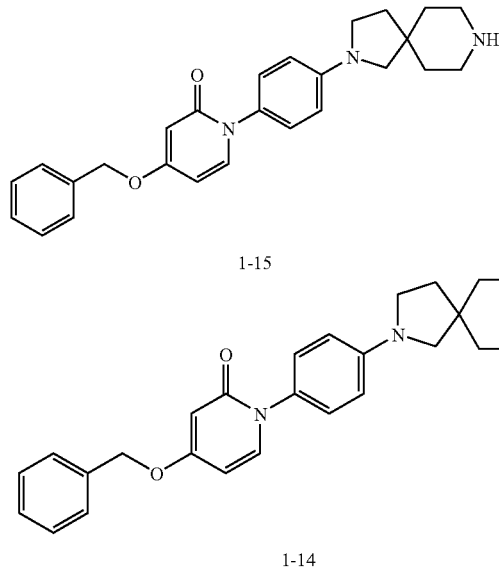

First compound 1-15 was converted to the free base (which corresponds to compound 1-13) by methods well known to a person skilled in the art. Then a reductive methylation was performed overnight at 50° C. on a mixture of compound 1-13 (1.5 g, 0.0036 mol) and paraform (1 g) in methanol (150 ml), with Pt/C 5% (0.5 g) as a catalyst in the presence of a thiophene solution (1.0 ml; 4% in DIPE). Afer uptake of H$_2$ (1 equivalent), the catalyst was filtered off and the filtrate was evaporated. The residue was crystallized from CH$_3$CN. The desired compound was filtered off. Yield: 1.2 g of compound 1-14 (78%).

Tables 1 to 4 list the compounds of Formula (I), which are prepared according to one of the above described examples.

TABLE 1

| Co. Nr. | Scheme | ----L | Salt forms |
|---|---|---|---|
| 1-5 | 1A | azetidine-spiro-piperidine-NH | |
| 1-12 | 1A | azetidine-spiro-piperidine-NH | •CF$_3$COOH |
| 1-8 | 1A | azetidine-spiro-piperidine-N-ethyl | |
| 1-9 | 1A | azetidine-spiro-piperidine-N-cyclopropyl | |
| 1-11 | 1A | azetidinone-spiro-piperidine-NH | |
| 1-6 | 1A | pyrrolidine-spiro-piperidine-NH | •CF$_3$COOH |
| 1-13 | 1A | pyrrolidine-spiro-piperidine-NH | |
| 1-15 | 1A | pyrrolidine-spiro-piperidine-NH | •2HCl (and •0.8H$_2$O) |

TABLE 1-continued
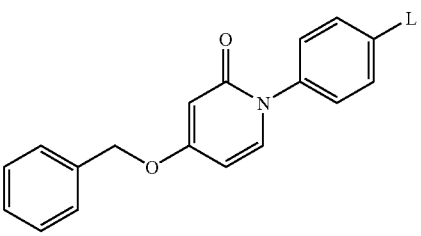
| Co. Nr. | Scheme | ----L | Salt forms |
|---|---|---|---|
| 1-7 | 1A | 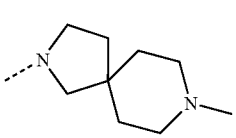 | •CF₃COOH |
| 1-14 | 1A | 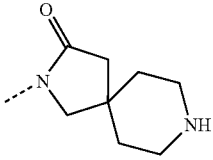 | |
| 1-10 | 1A |  | |
| 1-1 | 1A |  | •HCl |
| 1-2 | 1A | 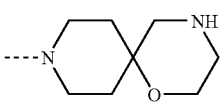 | |
| 1-3 | 1A | 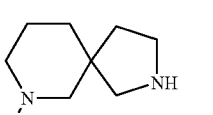 | |
| 1-4 | 1A | 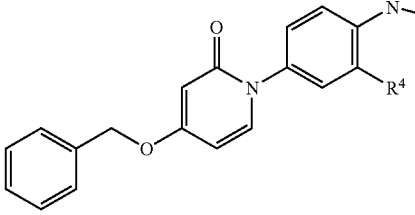 | •CF₃COOH |
TABLE 2
| Co. Nr. | Scheme | ----$R^3$ | ----$R^4$ | Salt forms |
|---|---|---|---|---|
| 2-1 | 2 | ----H | ----CH₃ | |
| 2-2 | 2 | ----H | ----O— | |
| 2-3 | 2 | ----H | ----Cl | |
| 2-4 | 2 | ----CH₃ | ----Cl | |
TABLE 3
| Co. Nr. | Ex. Nr. | —B—Y¹—Y²—Y³--- | Salt forms |
|---|---|---|---|
| 3-1 | 3A |  | |
| 3-2 | 3A | 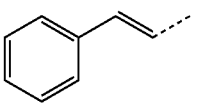 | |
| 3-3 | 3B | 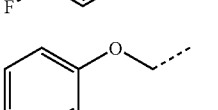 | |
| 3-4 | 3A | 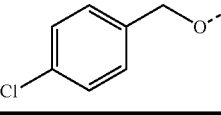 | |

TABLE 4

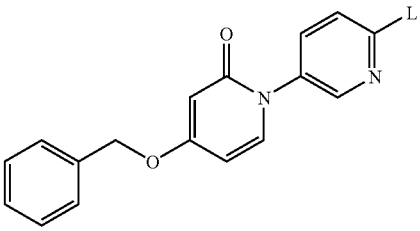

| Co. Nr. | Scheme | —L | Salt forms |
|---|---|---|---|
| 4-1 | 1B | ![structure] | |

Analytical Part

LCMS General Procedure A

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS spectrometer. The MS detector was configured with an electrospray ionization source. Nitrogen was used as the nebulizer gas. The source temperature was maintained at 140° C. Data acquisition was performed with MassLynx-Openlynx software.

LCMS General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS—Procedure 1

In addition to general procedure A: Reversed phase HPLC was carried out on an ACE-C18 column (3.0 μm, 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

LCMS—Procedure 2

In addition to general procedure B: Reversed phase HPLC was carried out on an Xterra MS C18 column (3.5 μm, 4.6× 100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 3

In addition to general procedure B: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 4

In addition to general procedure C: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Melting Points

For a number of compounds, melting points (m.p.) were determined with a DSC823e (Mettler-Toledo). Melting points were measured with a temperature gradient of 30° C./minute. Maximum temperature was 400° C. Values are peak values.

For a number of compounds, melting points (m.p.) were determined with a DSC822e (Mettler-Toledo). Melting points were measured with a temperature gradient of 10° C./minute. Final temperature was set at 300° C. Values are peak values.

For a number of compounds, melting points were determined in open capillary tubes on a Mettler FP62 apparatus. Melting points were measured with a temperature gradient of 10° C./minute. Maximum temperature was 300° C. The melting point was read from a digital display.

Values were obtained with experimental uncertainties that are commonly associated with this analytical method.

TABLE 5

Analytical data - Retention time ($R_t$ in minutes), $(MH)^+$ peak, LCMS procedure and melting points (m.p. is defined as melting point).

| Co. Nr. | $R_t$ | $(MH)^+$ | LCMS Procedure | m.p. (° C.) |
|---|---|---|---|---|
| 1-1 | 0.95 | 402 | 4 | |
| 1-2 | 4.95 | 430 | 2 | 141.5 (DSC823e) |
| 1-3 | 3.81 | 432 | 1 | |
| 1-4 | 1.02 | 416 | 4 | |
| 1-5 | 3.25 | 402 | 1 | 203.2 (Mettler FP 62) |
| 1-6 | 1.02 | 416 | 4 | |
| 1-7 | 3.77 | 416 | 1 | 236.3 (DSC822e) |
| 1-8 | 3.58 | 430 | 1 | |
| 1-9 | 5.13 | 442 | 1 | 276.5 (Mettler FP 62) |
| 1-10 | 2.78 | 430 | 1 | |
| 1-11 | 2.99 | 416 | 1 | |
| 1-12 | 3.35 | 402 | 1 | 231.0 (DSC822e) |
| 1-13 | 4.71 | 416 | 3 | 189.4 (DSC823e) |
| 1-14 | 1.05 | 430 | 4 | |
| 1-15 | 1.04 | 416 | 4 | |
| 2-1 | 3.49 | 416 | 1 | 164.6 (DSC822e) |
| 2-2 | 3.29 | 432 | 1 | |
| 2-3 | 3.72 | 436 | 1 | |
| 2-4 | 1.01 | 450 | 4 | |
| 3-1 | 3.65 | 398 | 1 | |
| 3-2 | 3.36 | 420 | 1 | |
| 3-3 | 3.08 | 402 | 1 | 292.7 (Mettler FP 62) |
| 3-4 | 4.94 | 436 | 2 | >300 (Mettler FP 62) |
| 4-1 | 2.88 | 403 | 1 | 198.9 (Mettler FP 62) |

C. Pharmacological Examples

The interaction of the compounds of Formula (I) with MCH-1 receptors was assessed in in vitro transient calcium ($Ca^{2+}$) mobilization assays in the fluorimetric imaging plate reader (FLIPR) format (Sullivan et al. 1999, Methods Mol Biol 114:125-133). In general, the natural agonist (MCH) is incubated with cells expressing the MCH-1 receptor, which elicits a concentration-dependent transient mobilization of $Ca^{2+}$ from internal stores. The interaction of the test compounds with the receptor is assessed in competition experiments. Various concentrations of the test compound are added to the incubation mixture containing the receptor-expressing cells and a submaximal concentration of MCH. The test compound in proportion to its antagonist potency and its concentration inhibits MCH-induced $Ca^{2+}$ mobilization.

Example C.1

Binding Experiment for MCH-1

Cell culture and membrane preparation. Chinese Hamster ovary cells (CHO) stably expressing the human MCH-1 receptor are grown in a 1:1 mixture of Dulbecco's Modified Eagles Medium (DMEM) and HAM's F12 medium including Glutamax™ (Invitrogen), supplemented with 10% heat-inactivated fetal bovine serum and 400 µg/ml geneticin.

$Ca^{2+}$ mobilization experiment for the MCH-1 receptor. Twenty-four hours before the experiment, MCH-1 receptor-expressing CHO cells are seeded in 20 µl (5,000 cells per well) into 384-well black wall, clear bottom microtiter plates (Costar). On the day of the experiment, 20 µl per well calcium assay kit containing 10 mM probenicide (Molecular Devices) is added. Cells are loaded for 90 min at 37° C. and 5% $CO_2$ in a cell culture incubator. After loading, 20 µl of serial dilutions of the test compound are added and cells are further incubated for 20 min at room temperature in the dark. After 20 min, 20 µl of a submaximal MCH concentration is added and changes in intracellular calcium are recorded directly in a FLIPR III apparatus (Molecular devices).

Data analysis and results. Data from assays in the presence of compound were calculated as a percentage of total $Ca^{2+}$-responses measured in the absence of test compound. Inhibition curves, plotting percent of total $Ca^{2+}$-responses versus the log value of the concentration of the test compound, were automatically generated, and sigmoidal inhibition curves were fitted using non-linear regression. The $pIC_{50}$ values of test compounds were derived from individual curves.

All compounds according to Formula (I) produced an inhibition of more than 50% ($pIC_{50}$) at a test concentration ranging between $10^{-6}$ M and $10^{-9}$ M in a concentration-dependent manner.

For a selected number of compounds, covering most of the various embodiments of Formula (I), the results of the in vitro studies are given in Table 6.

TABLE 6

Pharmacological data for compounds according to the invention.

| Compound Nr. | MCH-1 $pIC_{50}$ |
|---|---|
| 1-12 | 7.6 |
| 1-6 | 7.6 |
| 2-1 | 7.6 |
| 2-3 | 7.6 |
| 3-4 | 7.6 |
| 1-14 | 7.5 |
| 1-4 | 7.5 |
| 1-5 | 7.5 |
| 2-4 | 7.5 |
| 2-2 | 7.4 |
| 3-2 | 7.4 |
| 1-2 | 7.3 |
| 1-11 | 7.3 |
| 1-7 | 7.2 |
| 1-8 | 7.2 |
| 3-1 | 7.2 |
| 4-1 | 7.2 |
| 1-1 | 7.1 |
| 1-10 | 7.1 |
| 1-9 | 7.0 |
| 1-3 | 6.9 |
| 3-3 | 6.3 |

Example C.2

Determination of hERG-Reduction

The potential effects of the compounds according to the invention on the hERG-mediated membrane $K^+$ current were studied at single-cell level using the single electrode, whole-cell configuration of the patch clamp technique (Hamill, O. P., Marty, A., Neher, E., Sakmann, B. & Sigworth, F. J. (1981) Improved patch-clamp techniques for high-resolution current recording from cells and cell-free membrane patches. Pflügers Archiv. 391: 85-100).

HERG (human ether-à-go-go-related gene) encodes a potassium channel with biophysical properties similar to the rapidly activating delayed-rectifier $K^+$ current ($I_{Kr}$) in cardiac myocytes (Snyders, D. J. & Chaudhary, A. (1996). High affinity open channel block by dofetilide of HERG expressed in a human cell line. Molecular Pharmacology 49, 949-955 and Smith, P. L., Baukrowitz, T. & Yellen, G. (1996). The inward rectification mechanism of the HERG cardiac potassium channel. Nature 379, 833-836). This $I_{Kr}$ current contributes to the $K^+$ current responsible for the repolarization phase of the cardiac action potential. Blocking this current may prolong action potential duration and cause long QT-syndrome. The development of QT prolongation can lead to the occurrence of ventricular arrhythmias such as Torsades de Pointes which can result in sudden death.

An automated patch-clamp assay utilizing the PatchXpress 7000A system (Axon Instruments) was employed to assess the effect of test substances on HERG tail current.

Cells: A human embryonic kidney cell line (HEK293) with a stable transfection of HERG was used (Mohammad, S., Zhou, Z., Gong, Q. & January, C. T. (1997). Blockage of the HERG human cardiac K+ channel by the gastrointestinal prokinetic agent cisapride. American Journal of Physiology 273, H2534-H2538 and Zhou, Z., Gong, Q., Ye, B., Fan, Z., Makielski, J. C., Robertson, G. A. & January, C. T. (1998). Properties of HERG channels stably expressed in HEK 293 cells studied at physiological temperature. Biophysical Journal 74, 230-241). The cells were continuously kept in culture. Before use a cell suspension was prepared and immediately prior to experimentation, these cells were centrifuged at 1000 rpm for 1 minute, the supernatant was decanted and the cells were re-suspended in 150 µl of bath solution in a 1.5 ml eppendorf tube.

Solutions: The bath solution contained 137 mM NaCl, 4 mM KCl, 10 mM glucose, 10 mM HEPES, 1.8 mM $CaCl_2$ and 1 mM $MgCl_2$ (pH 7.4 with NaOH). The pipette solution contained 130 mM KCl, 5 mM EGTA, 10 mM HEPES, 5 mM MgATP and 1 mM $MgCl_2$ (pH 7.2 with KOH). Test compounds were dissolved in DMSO to obtain a stock solution of $10^{-2}$ M to $3 \times 10^{-1}$ M (final DMSO concentration: 0.3, 0.1 or 0.03%). Control (=bath solution+DMSO) and test solutions (=bath solution+DMSO+test compound) contained 0.3% or 0.1% DMSO.

Recording System: The PatchXpress system was primed with bath and pipette solution. A 16-well sealchip (Sealchip16, Aviva Biosciences Corp.) was loaded into the system and primed before preparing cells in the bath solution suspension. The eppendorf tube filled with cells, was placed into the designated position and the procedure commenced with the trituration and dispersion of cells into each recording chamber (well) of the sealchip. The PatchXpress system followed the general principles of conventional whole-cell patch-clamping.

Measurements: The HERG current was determined as the maximal tail current at −50 mV after a 4.8 second depolarization to +20 mV, starting from a holding potential of −80 mV. Each value represents the average current from 4 sequential voltage pulses. To determine the extent of block the residual current was compared with vehicle pre-treatment. The effect of the test compound on the HERG current was measured after 5 minutes of drug application. If more than 5% reduction of the HERG current can be observed, the test substance is considered to (partially) block the HERG current.

Control experiments: Time-matched vehicle control experiments were performed under identical conditions. Astemizole was used as a reference compound known to inhibit the HERG-mediated current at nanomolar concentrations.

TABLE 7

Comparison of hERG-reduction values.

| Compound | Structure | hERG-reduction (%) at 3 µM |
|---|---|---|
| Prior art compound (Banyu 2005/085200) | [structure] | 38.9% |
| Prior art compound (Banyu 2005/085200) | [structure] | 42.6% |
| Compound 1-7 | [structure] | −1.8% |

TABLE 7-continued

Comparison of hERG-reduction values.

| Compound | Structure | hERG-reduction (%) at 3 μM |
|---|---|---|
| Compound 1-12 | 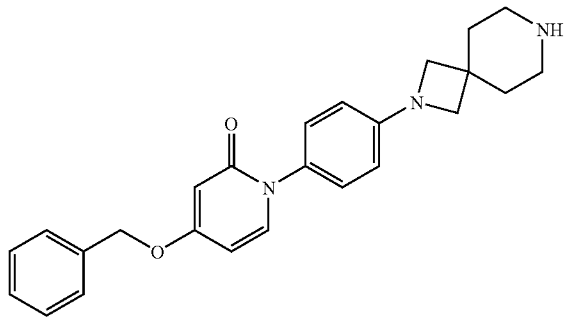 | 0.7% |
| Compound 2-1 | 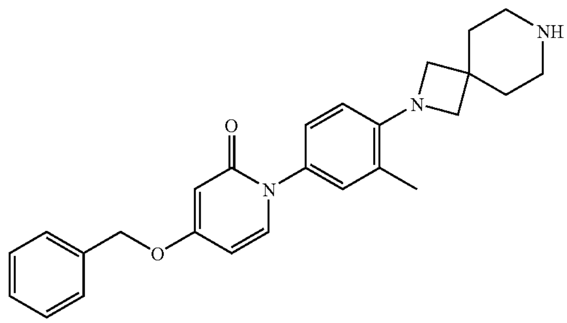 | 15.6% |

D. Composition Examples

"Active ingredient" (a.i.) as used throughout these examples relates to a final compound of formula (i), the pharmaceutically acceptable acid or base addition salts thereof, the stereochemically isomeric forms thereof, the N-oxide form thereof, a quaternary ammonium salt thereof and prodrugs thereof.

Example D.1

Oral Drops

500 Grams of the a.i. is dissolved in 0.5 l of 2-hydroxypropanoic acid and 1.5 l of the polyethylene glycol at 60–80° c. After cooling to 30–40° C. there are added 35 l of polyethylene glycol and the mixture is stirred well. Then there is added a solution of 1750 grams of sodium saccharin in 2.5 l of purified water and while stirring there are added 2.5 l of cocoa flavor and polyethylene glycol q.s. to a volume of 50 l, providing an oral drop solution comprising 10 mg/ml of a.i. The resulting solution is filled into suitable containers.

Example D.2

Oral Solution

9 Grams of methyl 4-hydroxybenzoate and 1 gram of propyl 4-hydroxybenzoate are dissolved in 4 l of boiling purified water. In 3 l of this solution are dissolved first 10 grams of 2,3-dihydroxybutanedioic acid and thereafter 20 grams of the a.i. The latter solution is combined with the remaining part of the former solution and 12 l 1,2,3-propanetriol and 3 l of sorbitol 70% solution are added thereto. 40 Grams of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the active ingredient per teaspoonful (5 ml). The resulting solution is filled in suitable containers.

Example D.3

Film-Coated Tablets

Preparation of Tablet Core

A mixture of 100 grams of the a.i., 570 grams lactose and 200 grams starch is mixed well and thereafter humidified with a solution of 5 grams sodium dodecyl sulfate and 10 grams polyvinylpyrrolidone in about 200 ml of water. The wet powder mixture is sieved, dried and sieved again. Then there is added 100 grams microcrystalline cellulose and 15 grams hydrogenated vegetable oil. The whole is mixed well and compressed into tablets, giving 10,000 tablets, each containing 10 mg of the active ingredient.

Coating

To a solution of 10 grams methyl cellulose in 75 ml of denaturated ethanol there is added a solution of 5 grams of ethyl cellulose in 150 ml of DCM. Then there are added 75 ml of DCM and 2.5 ml 1,2,3-propanetriol. 10 grams of polyethylene glycol is molten and dissolved in 75 ml of DCM. The latter solution is added to the former and then there are added 2.5 grams of magnesium octadecanoate, 5 grams of polyvinylpyrrolidone and 30 ml of concentrated color suspension and the whole is homogenated. The tablet cores are coated with the thus obtained mixture in a coating apparatus.

Example D.4

Injectable Solution 1.8 grams methyl 4-hydroxybenzoate and 0.2 grams propyl 4-hydroxybenzoate are dissolved in about 0.5 l of boiling water for injection. After cooling to about 50° C. there are added while stirring 4 grams lactic acid, 0.05 grams propylene glycol and 4 grams of the a.i. The solution is cooled to room temperature and supplemented with water for injection q.s. ad 1 l, giving a solution comprising 4 mg/ml of a.i. The solution is sterilized by filtration and filled in sterile containers.

The invention claimed is:

1. Compound according to Formula (I)

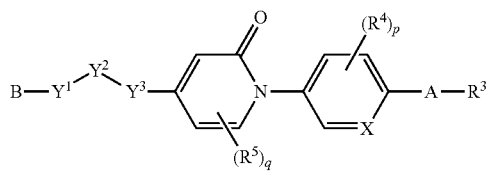

a pharmaceutically acceptable acid or base addition salt thereof, an N-oxide form thereof or a quaternary ammonium salt thereof, wherein:

A is a radical according to Formula (II)

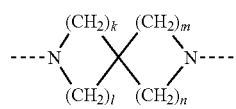

wherein k, l, m, n are each independently from each other, an integer equal to 0, 1, 2, 3, or 4, with the provision that (k+l) and (m+n) is equal to 2, 3, 4, or 5; wherein one of the —CH$_2$-moieties may be replaced by O; and wherein each of the —CH$_2$-moieties may be substituted with oxo;

X is C or N;

R$^3$ is selected from the group of hydrogen, C$_{1-5}$alkyl, C$_{3-6}$cycloalkyl, and C$_{1-5}$alkyloxycarbonyl;

R$^4$, R$^5$ are each, independently from each other, selected from the group of hydrogen, halo, cyano, hydroxy, amino, oxo, carboxyl, nitro, thio, formyl, C$_{1-3}$alkyl, and C$_{1-3}$alkyloxy;

p is an integer, equal to zero, 1, 2, or 3;

q is an integer, equal to zero, 1, 2, or 3;

Y$^1$, Y$^3$ are each, independently from each other, selected from the group of a single bond, O, NR$^7$, S, SO, and SO$_2$; wherein R$^7$ is selected from the group of hydrogen and C$_{1-3}$alkyl;

Y$^2$ is a saturated or unsaturated, straight or branched C$_{1-6}$-hydrocarbon radical, wherein one or more hydrogen atoms may optionally be replaced by a radical selected from the group of halo, cyano, hydroxy, amino, oxo, carboxyl, nitro, thio, and formyl;

B is a 6-membered ring containing zero, 1, 2 or 3 nitrogen atoms, optionally substituted with r substituents R$^6$, each independently from each other, selected from the group of halo, cyano, hydroxy, amino, oxo, carboxyl, nitro, thio, formyl, C$_{1-3}$alkyl, and C$_{1-3}$alkyloxy; and wherein r is an integer, equal to 1 or 2; or two substituents R$^6$ may be combined into a radical —CH$_2$CH$_2$CH$_2$— or —OCH$_2$O—;

alkyl is a straight or branched saturated hydrocarbon radical having the indicated number of carbon atoms; wherein the radical may optionally be substituted on one or more carbon atoms with one or more radicals selected from the group of halo, cyano, hydroxy, amino, oxo, carboxyl, nitro, thio, and formyl;

aryl is naphthyl or phenyl, each optionally substituted with 1, 2 or 3 substituents, each independently from each other selected from the group of halo, cyano, hydroxy, amino, oxo, carboxyl, nitro, thio, formyl, C$_{1-3}$alkyl, and C$_{1-3}$alkyloxy;

Het is a heterocyclic radical selected from the group of pyrrolidinyl; imida-zolidinyl; pyrazolidinyl; piperidinyl; piperazinyl; pyrrolyl; pyrrolinyl; imidazolinyl; pyrrazolinyl; pyrrolyl; imidazolyl; pyrazolyl; triazolyl; pyridinyl; pyridazinyl; pyrimidinyl; pyrazinyl; triazinyl; azepyl; di-azepyl; morpholinyl; thiomorpholinyl; furyl; thienyl; oxazolyl; isoxazolyl; thiazolyl; thiadiazolyl; isothiazolyl; dioxolyl; dithianyl; tetrahydrofuryl; tetrahydropyranyl; and oxadiazolyl; each Het optionally substituted with 1, 2 or 3 substituents, each independently from each other selected from the group of halo, cyano, hydroxy, amino, oxo, carboxyl, nitro, thio, formyl, C$_{1-3}$alkyl, and C$_{1-3}$alkyloxy; and halo is fluoro, chloro, bromo or iodo.

2. Compound according to claim 1, wherein k, l, m, n are each independently from each other, an integer equal to 1, 2, or 3, with the provision that (k+l) and (m+n) is equal to 2, 3, or 4.

3. Compound according to claim 1, wherein A is selected from the group of (a-1), (b-1), (b-3), (b-5), and (c-2)

(a-1)

(b-1)

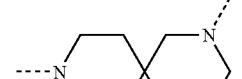

(c-2)

(b-3)

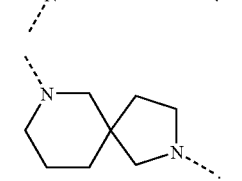

(b-5)

4. Compound according to claim 1, wherein A is a radical according to Formula (cc-2)

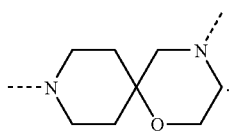
(cc-2)

5. Compound according to claim 1, wherein A is a radical according to (aa-1) or (bb-1)

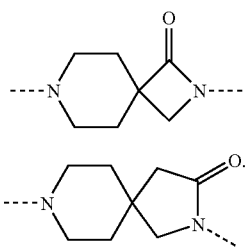
(aa-1)

(bb-1)

6. Compound according to claim 1, wherein $R^3$ is selected from the group of hydrogen, $C_{3-6}$cycloalkyl, and $C_{1-5}$alkyl.

7. Compound according to claim 1, wherein X is carbon or nitrogen.

8. Compound according to claim 1, wherein each of $R^4$ and $R^5$, independently from each other, are selected from the group of hydrogen, halo, $C_{1-3}$alkyl, and $C_{1-3}$alkyloxy.

9. Compound according to claim 1, wherein p is zero or 1.

10. Compound according to claim 1, wherein q is zero.

11. Compound according to claim 1, wherein $Y^1$ and $Y^3$ are each, independently from each other, selected from the group of a single bond and O.

12. Compound according to claim 1, wherein $Y^2$ is selected from the group of —CH$_2$—, —CH$_2$CH$_2$—, and —CH=CH—.

13. Compound according to claim 1, wherein B is phenyl.

14. Compound according to claim 13, wherein B is substituted with one halo substituent.

15. Compound according to claim 1, wherein the moiety B—$Y^1$—$Y^2$—$Y^3$ is selected from the radicals (a1-2), (a1-3) and (a1-5), optionally substituted with r substituents $R^6$

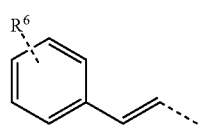
(a1-2)

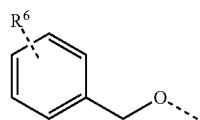
(a1-3)

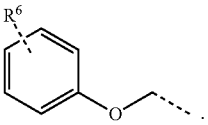
(a1-5)

16. Compound according to claim 1, a pharmaceutically acceptable acid or base addition salt thereof, an N-oxide form thereof or a quaternary ammonium salt thereof, wherein:

k, l, m, n are each independently from each other, an integer equal to 1, 2, or 3 with the provision that (k+l) and (m+n) is equal to 2, 3, or 4; wherein one of the —CH$_2$-moieties may be replaced by O; and wherein each of the —CH$_2$-moieties may be substituted with oxo;

X is C or N;

$R^3$ is selected from the group of hydrogen, $C_{3-6}$cycloalkyl, and $C_{1-5}$alkyl;

$R^4$, $R^5$ are each, independently from each other, selected from the group of hydrogen, halo, $C_{1-3}$alkyl, and $C_{1-3}$alkyloxy;

p is an integer, equal to zero, or 1;

q is an integer, equal to zero;

$Y^1$, $Y^3$ are each, independently from each other, selected from the group of a single bond or O;

$Y^2$ is a saturated or unsaturated, straight or branched $C_{1-6}$-hydrocarbon radical; and B is phenyl, optionally substituted with one halo substituent $R^6$.

17. Compound according to claim 1, a pharmaceutically acceptable acid or base addition salt thereof, an N-oxide form thereof or a quaternary ammonium salt thereof, wherein:

A is selected from the group of (a-1), (b-1), (b-3), (b-5), and (c-2),

(a-1)

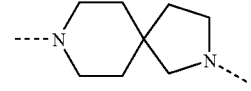
(b-1)

(c-2)

X is C or N;

$R^3$ is selected from the group of hydrogen, $C_{3-6}$cycloalkyl, and $C_{1-5}$alkyl;

$R^4$, $R^5$ are each, independently from each other, selected from the group of hydrogen, halo, $C_{1-3}$alkyl, and $C_{1-3}$alkyloxy;

p is an integer, equal to zero, or 1;

q is an integer, equal to zero; the moiety B—$Y^1$—$Y^2$—$Y^3$ is selected from the radicals (a1-2), (a1-3) and (a1-5), optionally substituted with r substituents $R^6$

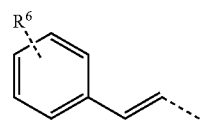
(a1-2)

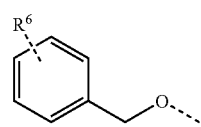
(a1-3)

-continued

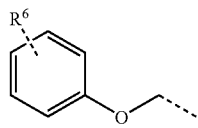
(a1-5)

R[6] is a halo substituent; and wherein r is an integer, equal to 1 or 2.

18. Compound according to claim 1, a pharmaceutically acceptable acid or base addition salt thereof, an N-oxide form thereof or a quaternary ammonium salt thereof, wherein:

A is selected from the group of (a-1), (b-1), (b-3), (b-5), and (c-2),

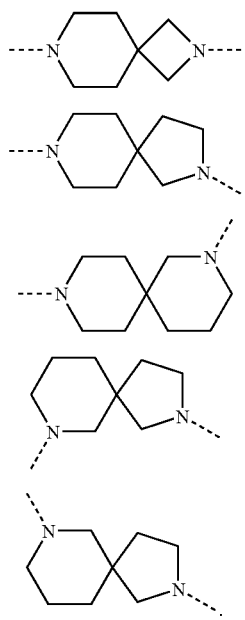

X is C or N;
R[3] is selected from the group of hydrogen, $C_{3-5}$cycloalkyl, and $C_{1-3}$alkyl;
R[4], R[5] are each, independently from each other, selected from the group of hydrogen, halo, $C_{1-3}$alkyl, and $C_{1-3}$alkyloxy;
p is an integer, equal to zero, or 1;
q is an integer, equal to zero;
Y[1], Y[3] are each, independently from each other, selected from the group of a single bond or O;
Y[2] is a saturated or unsaturated, straight or branched $C_{1-6}$-hydrocarbon radical; and
B is phenyl, optionally substituted with one halo substituent R[6].

19. Compound according to claim 1, a pharmaceutically acceptable acid or base addition salt thereof, an N-oxide form thereof or a quaternary ammonium salt thereof, wherein:

A is selected from the group of (a-1), or (b-1);

(a-1)

(b-1)

X is C;
R[3] is a methyl;
R[4], R[5] are each, independently from each other, selected from the group of hydrogen, or halo;
p is an integer, equal to zero, or 1;
q is an integer, equal to zero;
Y[1] is a single bond;
Y[3] is O;
Y[2] is a $CH_2$; and
B is phenyl.

20. Pharmaceutical composition comprising a pharmaceutically acceptable carrier or diluent and, as active ingredient, a therapeutically effective amount of a compound according to claim 1.

21. Pharmaceutical composition according to claim 20, wherein it is in a form suitable to be orally administered.

22. Pharmaceutical composition according to claim 21, wherein it comprises further one or more other compounds selected from the group of antidepressants, anxiolytics and antipsychotics.

23. Pharmaceutical composition according to claim 22, wherein it comprises further one or more other compounds selected from the group of lipid-lowering compounds.

* * * * *